United States Patent
Soane et al.

(10) Patent No.: US 12,325,841 B2
(45) Date of Patent: Jun. 10, 2025

(54) ARTICLES OF MANUFACTURE COMPRISING NANOCELLULOSE ELEMENTS

(71) Applicant: Soane Materials LLC, Miami, FL (US)

(72) Inventors: David S. Soane, Coral Gables, FL (US); Allison Hope Greene, Reno, NV (US); Juan Sebastian Colmenares, Reno, NV (US)

(73) Assignee: Soane Materials LLC, Miami, FL (US)

( * ) Notice: Subject to any disclaimer, the term of this patent is extended or adjusted under 35 U.S.C. 154(b) by 0 days.

(21) Appl. No.: 18/825,369

(22) Filed: Sep. 5, 2024

(65) Prior Publication Data

US 2025/0066699 A1    Feb. 27, 2025

Related U.S. Application Data

(63) Continuation of application No. 18/588,964, filed on Feb. 27, 2024, which is a continuation of application No. 18/123,476, filed on Mar. 20, 2023, now Pat. No. 11,932,829, which is a continuation of application No. 17/834,521, filed on Jun. 7, 2022, now Pat. No. 12,122,980.

(60) Provisional application No. 63/309,730, filed on Feb. 14, 2022, provisional application No. 63/219,686, filed on Jul. 8, 2021, provisional application No. 63/208,577, filed on Jun. 9, 2021.

(51) Int. Cl.
| | |
|---|---|
| C11D 17/04 | (2006.01) |
| C11D 11/00 | (2006.01) |
| D21H 11/12 | (2006.01) |
| D21H 11/14 | (2006.01) |
| D21H 11/18 | (2006.01) |
| D21H 17/06 | (2006.01) |
| D21H 17/07 | (2006.01) |
| D21H 17/09 | (2006.01) |
| D21H 17/14 | (2006.01) |
| D21H 17/20 | (2006.01) |
| D21H 17/26 | (2006.01) |
| D21H 17/34 | (2006.01) |
| D21H 17/36 | (2006.01) |
| D21H 21/08 | (2006.01) |
| D21H 21/10 | (2006.01) |

(52) U.S. Cl.
CPC .......... *C11D 17/042* (2013.01); *C11D 17/045* (2013.01); *D21H 11/12* (2013.01); *D21H 11/14* (2013.01); *D21H 11/18* (2013.01); *D21H 17/06* (2013.01); *D21H 17/07* (2013.01); *D21H 17/14* (2013.01); *D21H 17/20* (2013.01); *D21H 17/26* (2013.01); *D21H 17/34* (2013.01); *D21H 17/36* (2013.01); *D21H 21/08* (2013.01); *D21H 21/10* (2013.01); *C11D 2111/12* (2024.01); *C11D 2111/14* (2024.01)

(58) Field of Classification Search
None
See application file for complete search history.

(56) References Cited

U.S. PATENT DOCUMENTS

| | | | |
|---|---|---|---|
| 2,261,091 | A | 10/1941 | Francis |
| 4,341,807 | A | 7/1982 | Turbak et al. |
| 4,378,381 | A | 3/1983 | Turbak et al. |
| 4,481,076 | A | 11/1984 | Herrick |
| 5,998,349 | A | 12/1999 | Guillou |
| 6,291,558 | B1 | 9/2001 | Raskin et al. |
| 8,372,320 | B2 | 2/2013 | Gardner et al. |
| 8,722,143 | B2 | 5/2014 | Werner et al. |
| 8,785,158 | B2 | 7/2014 | Koivunen et al. |
| 9,103,069 | B2 | 8/2015 | Graveson et al. |
| 9,121,111 | B2 | 9/2015 | Turner et al. |
| 9,133,578 | B2 | 9/2015 | Ruda et al. |
| 9,187,848 | B2 | 11/2015 | Graveson |
| 9,237,831 | B1 | 1/2016 | Luu et al. |
| 9,273,432 | B2 | 3/2016 | Jogikalmath et al. |
| 9,371,401 | B2 | 6/2016 | Graveson et al. |
| 9,469,696 | B2 | 10/2016 | Laukkanen et al. |
| 9,512,543 | B2 | 12/2016 | Turner et al. |
| 9,556,325 | B2 | 1/2017 | Tchang Cervin et al. |
| 9,700,915 | B2 | 7/2017 | Ruda |
| 9,767,944 | B2 | 9/2017 | Galland et al. |
| 10,035,890 | B2 | 7/2018 | Kochumalayil et al. |
| 10,087,580 | B2 | 10/2018 | Ben et al. |
| 10,099,192 | B2 | 10/2018 | Carrick et al. |
| 10,100,269 | B2 | 10/2018 | Fernandez-Prieto et al. |

(Continued)

FOREIGN PATENT DOCUMENTS

| | | |
|---|---|---|
| CN | 103435850 A | 12/2013 |
| CN | 106318177 A | 1/2017 |

(Continued)

OTHER PUBLICATIONS

Propylene Glycol, Wikipedia, 2018 [retrieved from the internet on Jul. 27, 2022 at <https://en.wikipedia.org/wiki/Propyleneglycol>.

(Continued)

*Primary Examiner* — Dennis R Cordray
(74) *Attorney, Agent, or Firm* — Elmore Patent Law Group, P.C.; Mahreen Chaudhry Hoda; Carolyn S. Elmore

(57) ABSTRACT

The present invention provides formulations comprising a suspension of nanocellulose (NC) elements and a drying/dispersal additive selected from the group consisting of temperature-responsive polymers, small molecule additives in volatile systems, and blocking agents and methods of preparing such formulations, and further provides NC-containing materials, composite materials and useful articles of manufacture made therefrom.

27 Claims, No Drawings

(56) References Cited

U.S. PATENT DOCUMENTS

| | | | |
|---|---|---|---|
| 10,294,371 | B2 | 5/2019 | Gane et al. |
| 10,299,501 | B2 | 5/2019 | Tan et al. |
| 10,301,774 | B2 | 5/2019 | Gane et al. |
| 10,435,482 | B2 | 10/2019 | Windebank et al. |
| 10,669,384 | B2 | 6/2020 | Menendez Gonzalez et al. |
| D893,800 | S | 8/2020 | Stern |
| 10,736,790 | B2 | 8/2020 | Bothra et al. |
| 10,794,006 | B2 | 10/2020 | Phipps et al. |
| 10,907,020 | B2 | 2/2021 | Johansson et al. |
| 10,907,084 | B2 | 2/2021 | Pearl et al. |
| 11,001,644 | B2 | 5/2021 | Windebank et al. |
| 11,045,397 | B2 | 6/2021 | Stern et al. |
| 11,091,877 | B2 | 8/2021 | Johansson et al. |
| 11,141,885 | B2 | 10/2021 | Hendrix et al. |
| 11,390,793 | B2 | 7/2022 | Pearl et al. |
| 11,485,797 | B2 | 11/2022 | Williams et al. |
| 11,549,216 | B2 | 1/2023 | Pomeroy et al. |
| 2011/0259537 | A1 | 10/2011 | Husband et al. |
| 2011/0290149 | A1 | 12/2011 | Beck et al. |
| 2014/0079931 | A1 | 3/2014 | Berglund et al. |
| 2015/0273420 | A1 | 10/2015 | Capron et al. |
| 2015/0297371 | A1 | 10/2015 | Zhang et al. |
| 2017/0014313 | A1 | 1/2017 | Stern et al. |
| 2017/0183555 | A1 | 6/2017 | Lillandt et al. |
| 2017/0210826 | A1 | 7/2017 | Nelson et al. |
| 2018/0094383 | A1 | 4/2018 | Bilodeau et al. |
| 2018/0298113 | A1 | 10/2018 | Nelson et al. |
| 2019/0185638 | A1 | 6/2019 | Retsina et al. |
| 2019/0224083 | A1 | 7/2019 | Kawasaki et al. |
| 2020/0063368 | A1 | 2/2020 | Parker et al. |
| 2020/0109516 | A1 | 4/2020 | Retsina et al. |
| 2021/0155775 | A1 | 5/2021 | Banerjie et al. |
| 2021/0221919 | A1 | 7/2021 | Nelson et al. |
| 2021/0277151 | A1 | 9/2021 | Nelson et al. |
| 2021/0330519 | A1 | 10/2021 | Monroe et al. |
| 2021/0340706 | A1 | 11/2021 | Nelson et al. |
| 2021/0395493 | A1 | 12/2021 | Herd et al. |
| 2022/0073705 | A1 | 3/2022 | Nelson |
| 2022/0127788 | A1 | 4/2022 | Nelson |
| 2022/0389261 | A1 | 12/2022 | Koppolu et al. |
| 2022/0403301 | A1 | 12/2022 | Soane et al. |
| 2022/0412010 | A1 | 12/2022 | Soane et al. |
| 2023/0002972 | A1 | 1/2023 | Retsina et al. |
| 2023/0071816 | A1 | 3/2023 | Herd et al. |
| 2023/0227758 | A1 | 7/2023 | Soane et al. |

FOREIGN PATENT DOCUMENTS

| | | |
|---|---|---|
| CN | 112089685 A | 12/2020 |
| WO | 2020227816 A1 | 11/2020 |
| WO | 2022261103 A1 | 12/2022 |

OTHER PUBLICATIONS

"Advancing Commercialization of Nanocellulose: Critical Challenges Workshop Report", Presentation, Alliance for Pulp & Paper Technology Innovation, Mar. 2020, 1-51.
"Communication from the Commission to the European Parliament, the Council, the European Economic and Social Committee and the Committee of the Regions", COM(2018) 28 final, Jan. 16, 2018.
"HSMG Receives BfR Approval for the Use of Protean in Paper-Based Food Packaging", HSMG LLC Press release dated Jul. 9, 2020.
"HSMG Receives Notice of Allowance From United States Patent and Trademark Office", HSMG LLC Press release dated Mar. 22, 2021, 1.
"Manufacturing: Materials and processing", Polymer Sci. and Engineering: The Shifting Research Frontiers (1994) Chapter 3.
"Microfibrillated Cellulose at a Glance: Characteristics and Potential Applications", Exilva Marketing literature—Borregaard, 1-32.
"Natural Fibers and their Composites", Book, Tribology of Natural Fiber Polymer Composites, Chap. 1https://doi.org/10.1533/9781845695057.1, Mar. 27, 2014, 1-58.
"Protean OGR Barrier", Marketing literature—HS Manufacturing Group, Apr. 1, 2020, 1-2.
"Rosin Factory", Web page, https://www.rosin-factory.com/rosin-chemistry/, 1-3.
"Solenis Backgrounder", Marketing literature—Solenis.
"Solenis Helps Major Brand owner Meet Water and Oil Penetration Resistance in Thermoformed Molded Fiber Trays", Marketing Literature—Solenis.
"Table—Pulp Spot Pricing", Oct. 30, 2014.
Abdelmouleh, M. , et al., "Modification of Celluosic Fibres with Functionalised Silanes: Development of Surface Properties", Int. J. Adhesion Adhesives, vol. 24doi:10.1016/S0143-7496(03)00099-X, 43-54.
Ai, B. , et al., "Biodegradable Cellulose Film Prepared From Banana Pseudo-Stem Using and Ionic Liquid for Mango Preservation", Frontiers in Plant Sci., vol. 12, Art. 625878.
Ang, S. , et al., "Cellulose Nanofiber Diameter Distributions from Microscopy Image Analysis: Iffect of Measurement Statistics and Operator", Cellulose, https://doi.org/10.1007/s10570-020-03058-0(0123456789().,-volV() 0123458697().,-volV).
Arthanareeswaran, G. , et al., "Effect of Silica Particles on Cellulose Acetate Blend Ultrafiltration membranes: Part I", Separ. Purific. Tech., vol. 64DOI: 10.1016/j.seppur.2008.08.010, 38-47.
Arun, R., et al., "Biodegradable Nano Composite Reinforced with Cellulose Nano Fiber from Coconut Industry Waste for Replacing Synthetic Plastic Food Packaging", Chemosphere, vol. 291, 132786 (2022), https://doi.org/10.1016/j.chemosphere.2021.132786.
Bao, C., "Cellulose Acetate / Plasticizer Systems: Structure, Morphology and Dynamics", HAL Open Science, https://theses.hal.science/tel-01186696, 1-199 (2015).
Beaumont, M., et al., "Cellulose Nanofibrils: From Hydrogels to Aerogels", Cellulose Science and Technology.: Chemistry, Analysis, and Applications, First Edition, 277-339 (2019).
Butchosa, N., et al., "Water Redispersible Cellulose Nanofibrils Adsorbed with Carboxymethyl Cellulose", Cellulose, 21, 4349-4358 (2014) DOI 10.1007/s10570-014-0452-7.
Chu, Y., et al., "Dispersion Properties of Nanocellulose: A Review", J. Carbo. Polymers, 116892, 1-65 (2020).
Cindradewi, A., et al., "Preparation and Characterization of Cellulose Acetate Film Reinforced with Cellulose Nanofibril", Polymers, vol. 13, 1-14 (2021).
Corkery, M., "Your Foam Coffee Cup is Fighting for Its Life", New York Times, https://www.nytimes.com/2020/02/10/business/dart-foam-recycling.html, 1-17 (2020).
Costa, V., et al., "Hydrophobicity Improvement of Cellulose Nanofibrils Films by Stearic Acid and Modified Precipitated Calcium Carbonate Coating", J. Mater. Sci., vol. 57, 11443-11459 (2022).
Cragg, S., "Glycol Ethers: Ethers of Propylene, Butylene Glycols, and Other Glycol Derivatives", Patty's Toxicology, 6th Ed., vol. 4, Chap. 65, 789-877 (2012).
Cywar, R., et al., "Bio-Based Polymers with Performance-Advantaged Properties", Materials, vol. 7, 83-103 (2022) https://doi.org/10.1038/s41578-021-00363-3.
Deeth, H., "Optimum Thermal Processing for Extended Shelf-Life (ESL) Milk", Foods 2017, 6, 102, doi:10.3390/foods6110102, 1-21.
Deng, S., et al., "Hydrophobic Cellulose Films with Excellent Strength and Toughness via Ball Milling Activated Acylation of Microfibrillated Cellulose", Carbohydrate Polymers, 1-26 (2016), http://dx.doi.org/doi:10.1016/j.carbpol.2016.07.101.
Ding, B., et al., "Conversion of an Electrospun Nanofibrous Cellulose Acetate Mat from a Super-Hydrophilic to Super-Hydrophobic Surface", Nanotech., vol. 17, 4332-4339 (2006).
Domjan, A., et al., "Understanding of the Plasticizing Effects of Glycerol and PEG 400 on Chitosan Films Using Solid-State NMR Spectroscopy", Macromolecules, vol. 42, 4667-4673 (2009), DOI: 10.1021/ma8021234.
Elliott, T., et al., "European Union's Plastic Strategy and an Impact Assessment of the Proposed Directive on Tackling Single-Use Plastics Items", Plastic Waste and Recycling, ISBN 978-0-12-817880-5, https://doi.org/10.1016/B978-0-12-817880-5.00024-4, 601-633 (2020).

(56) References Cited

OTHER PUBLICATIONS

Espinosa, S., et al., "Isolation of Thermally Stable Cellulose Nanocrystals by Phosphoric Acid Hydrolysis", Biomacromolecules, vol. 14, 1223-1230 (2013) dx.doi.org/10.1021/bm400219u.
Foster, E., et al., "Current Characterization Methods for Cellulose Nanomaterials", Chem. Soc. Rev., vol. 47, No. 8, 2511-3006.
Frank, B., "Water Absorptiveness of Sized (Non-Bibulous) Paper, Paperboard, and Corrugated Fiberboard (Cobb Test) (Proposed Revision of T 441 om-09)", Draft TAPPI Standard, 1-18.
Frey, M., "Electrospinning Cellulose and Cellulose Derivatives", Polymer Reviews, vol. 48, 378-391 (2008).
Fujisawa, S., "Material Design of Nanocellulose/Polymer Composites via pickering Emulsion Templating", Polymer J., vol. 53, 103-109 (2021), https://doi.org/10.1038/s41428-020-00408-4.
Fujisawa, S., et al., "Nanocellulose-Stabilized Pickering Emulsions and their Applications", Sci. Tech. Adv. Mater., vol. 18, No. 1https://doi.org/10.1080/14686996.2017.1401423, 959-971.
Furtwengler, P., et al., "Renewable Polyols for Advanced Polyurethane Foams from Diverse Biomass Resources", Polym. Chem., vol. 9, 4258-4287 (2018), DOI: 10.1039/c8py00827b.
Gardner, D., et al., "Sustainable Nanomaterials from Forest Products: UMaine Perspective", Slide Presentation, 1-22.
George, J., et al., "Cellulose Nanocrystals: Synthesis, Functional Properties, and Applications", Nanotechnol. Sci. Appl., vol. 8, 45-54 (2015), doi:10.2147/NSA.S64386.
Geyer, R., et al., "Production, Use, and Fate of All Plastics Ever Made", Sci. Adv., 3(7), 1-5 (2017) e1700782.
Grunert, M., et al., "Nanocomposites of Cellulose Acetate Butyrate Reinforced with Cellulose Nanocrystals", J. Polymers Environ., vol. 10, Nos. 1/2, 27-30 (2002).
Guan, Q., et al., "Lightweight, Tough, and Sustainable Cellulose Nanofiber-Derived Bulk Structural Materials with Low Thermal Expansion Coefficient", Sci. Adv., vol. 6, No. 18, 1-13 (2020) DOI: 10.1126/sciadv.aaz1114.
Guo, A., et al., "A Review on the Application of Nanocellulose in Cementitious Materials", Nanomaterials (Basel), 10(12): 2476, 1-38, (2020), doi: 10.3390/nano10122476.
Hao, W., et al., "A Review on Nanocellulose as a Lightweight Filler of Polyolefin Composites", Carbohydrate Polymers (2020), 1-49, doi: https://doi.org/10.1016/j.carbpol.2020.116466.
He, M., et al., "Controllable Stearic Acid Crystal Induced High Hydrophobicity on Cellulose Film Surface", Appl. Mater. Interfaces, 5, 585-591 (2013), doi.org/10.1021/am3026536.
Heinze, T., et al., "Esterification of Polysaccharides", Book, e-ISBN 3-540-32112-8, 1-240 (2006), DOI 10.1007/b98412.
Heyn, A., "The Elementary Fibril and Supermolecular Structure of Cellulose in Soft Wood Fiber", J. Ultrastructure Res., vol. 26, 52-68 (1969).
Hjelt, T., et al., "Foam Forming of Fiber Products: A Review", J. Disp. Sci. Technol., vol. 43, No. 10, 1462-1497 (2022), https://doi.org/10.1080/01932691.2020.1869035.
Hsieh, Y., "Cellulose Nanofibers: Electrospinning and Nanocellulose Self-Assemblies", Adv. Green Composites, 67-96 (2018).
Huang, S., et al., "Cellulose Nanofibers/Polyvinyl Alcohol Blends as an Efficient Coating to Improve the Hydrophobic and Oleophobic Properties of Paper", Scientific Reports, 12:16148, 1-10 (2022), https://doi.org/10.1038/s41598-022-20499-8.
Ilyas, R., et al., "Oxygen Permeability Properties of Nanocellulose Reinforced Biopolymer Nanocomposites", Materials Today, Proceedings 52, 2414-2419 (2022), https://doi.org/10.1016/j.matpr.2021.10.420.
Ioelovich, M., "Adjustment of Hydrophobic Properties of Cellulose Materials", Polymers, 13, 1241, 1-11 (2021), https://doi.org/10.3390/polym13081241.
Jain, S., et al., "Cellulose Derivatives as Thermoresponsive Polymer: An Overview", J. Appl. Pharmaceut. Sci., vol. 3, No. 12, 139-144 (2013), DOI: 10.7324/JAPS.2013.31225.
Jimenez-Saelices, C., et al., "Spray Freeze-Dried Nanofibrillated Cellulose Aerogels With Thermal Superinsulating Properties", J. Carbo. Polymers, 1-30 (2016) http://dx.doi.org/doi:10.1016/j.carbpol.2016.09.068.
Jongaroontaprangsee, S., et al., J. Carbo. Polym., https://doi.org/10.1016/j.carbpol.2018.04.008, Jan. 4, 2018, 1-33.
Kalia, S., et al., "Cellulose Fibers: Bio- and Nano-Polymer Composites", Book, e-ISBN 978-3-642-17370-7, 1-743 (2011) DOI 10.1007/978-3-642-17370-7.
Kalia, S., et al., "Nanofibrillated Celluose: Surface Modification and Potential Applications", Colloid Polym. Sci., (2013) DOI 10.1007/s00396-013-3112-9.
Khalil, A., et al., "Production and Modification of Nanofibrillated Cellulose Using Various Mechanical Processes: A Review", Carbo. Polymers, 99, 649-665 (2014), http://dx.doi.org/10.1016/j.carbpol.2013.08.069.
Kiessling, T., et al., "What Potential Does the EU Single-Use Plastics Directive Have for Reducing Plastic Pollution at Coastlines and Riversides? An Evaluation Based on Citizen Science Data", Wast Management, 164, 106-118 (2023), https://doi.org/10.1016/j.wasman.2023.03.042.
Kim, G., et al., "Effect of Polyethylene Glycol, Triacetin and Glycerin on the Cellulose Acetate Plasticizing", Polymer (Korea), vol. 39, No. 4, 649-654 (2015), http://dx.doi.org/10.7317/pk.2015.39.4.649.
Kim, J., et al., "Fracture, Fatigue, and Friction of Polymers in Which Entanglements Greatly Outnumber Cross-Links", Science, vol. 374, 212-216 (2021).
Kim, S., et al., "Plasticizing Effect and Mechanical Properties of Polyethylene Glycol (PEG200), Triacetin (TA) on Cellulose Acetate/Polyethylene Glycol (PEG600)", Polymer (Korea), vol. 41, No. 2, 242-249 (2017), https://doi.org/10.7317/pk.2017.41.2.242.
Klebert, S., et al., "Modification of Cellulose Acetate with Oligomeric Polycaprolactone by Reactive Processing: Efficiency, Compatibility, and Properties", J. Appl. Polymer Sci., 3256-3263 (2009), DOI: 10.1002/app.30187.
Kumar, V., et al., "Comparison of Nano- and Microfibrillated Cellulose Films", Cellulose, 21, 3443-3456 (2014), DOI 10.1007/s10570-014-0357-5.
Lam, E., et al., "Preparation and Surface Functionalization of Carboxylated Cellulose Nanocrystals", Nanomaterials, vol. 11, 1641, 1-32 (2021), https://doi.org/10.3390/nano11071641.
Lavoine, N., et al., "Microfibrillated Cellulose—Its Barrier Properties and Applications in Cellulosic Materials: A Review", Carbohydrate Polymers, vol. 90, 735-764 (2012), http://dx.doi.org/10.1016/j.carbpol.2012.05.026.
Lavoine, N., et al., "Nanocellulose-Based Foams and Aerogels: Processing, Properties, and Applications", J. Mater. Chem. A, vol. 5, 16105-16117 (2017).
Lavric, G., et al., "Functional Nanocellulose, Alginate and Chitosan Nanocompoistes Designed as Active Film Packaging Materials", Polymers, vol. 13, No. 2523, 1-15 (2021), https://doi.org/10.3390/polym13152523.
Lease, J., et al., "Esterificatino of Cellulose with Lolng Fatty Acid Chain Through Mechanochemical Method", Polymers, vol. 13, 1-12 (2021), https://doi.org/10.3390/polym13244397.
Levy, I., et al., "Recombinant Cellulose Crosslinking Protein: A Novel Paper-Modification Biomaterial", Cellulose, vol. 9, 91-98 (2002).
Li, M., et al., "Recent Advancements of Plant-Based Natural Fiber-Reinforced Composites and Their Applications", Composites Part B: Engineering, vol. 200, 1-52 (2020), https://doi.org/10.1016/j.compositesb.2020.108254.
Li, Y., et al., "Effects of Emulsion Droplet Size on the Structure of Electrospun Ultrafine Biocomposite Fibers with Cellulose Nanocrystals", Biomacromol., vol. 14, 3801-3807 (2013), dx.doi.org/10.1021/bm400540v.
Liu, J., et al., "Preparation and Characterization of CarboxymethylCellulose Hydrogel Fibers", J. Eng. Fibers Fabrics, vol. 13, Iss. 3, 6-13 (2018).

(56) References Cited

OTHER PUBLICATIONS

Liu, Y., et al., "Comparative Study of Ultra-Lightweight Pulp Foams Obtained from Various Fibers and Reinforced by MFC", Carbohyd. Polymers, 1-12 (2017) https://doi.org/10.1016/j.carbpol.2017.10.078.
Malik, S., et al., "Electrospun Cellulose Composite Nanofibers and their Biotechnological Applications", Nanotech. Paper Wood Eng., Chap. 15, 329-348 (2022).
Misran, E., et al., "Preparation and Characterisation of Electrospun Composite Nanofibre Polyvinyl Alcohol/Nanofibrillated Cellulose Isolated from Oil Palm Empty Fruit Bunches", BioResources, 15(4), 7906-7917 (2020).
Missoum, K., et al., "Nanofibrillated Cellulose Surface Modification: A Review", Materials, vol. 6, 1745-1766 (2013) doi:10.3390/ma6051745.
Missoum, K., et al., "Water Redispersible Dried Nanofibrillated Cellulose by Adding Sodium Chloride", Biomacromolecules, vol. 13, dx.doi.org/10.1021/bm301378n, 4118-4125 (2012).
Mohammadkazemi, F., et al., "Manufacturing of Bacterial Nano-Cellulose Reinforced Fiber-Cement Composites", Const. Bldg. Mat 101, 958-964 (2015), http://dx.doi.org/10.1016/j.conbuildmat.2015.10.093.
Moser, C., et al., "Improved Dispersibility of Once-Dried Cellulose Nanofibers in the Presence of Glycol", Nordic Pulp & Paper Res. J., 1-4 (2018), https://doi.org/10.1515/npprj-2018-0054.
Nakagaito, A., et al., "Cellulose-Nanofiber-Based Materials", Cellulose Based Composites: New Green Nanomaterials, First Edition, Published by Wiley-VCH Verlag GmbH & Co. KGaA, 1-26 (2014).
Nasution, H., et al., "Crosslinking Agent for on Cellulose-Based Hydrogels", Retrieved from https://encyclopedia.pub/entry/27717, 1-15.
Nasution, H., et al., "Hydrogel and Effects of Crosslinking Agent on Cellulose-Based Hydrogels: A Review", Gels, vol. 8, 568https://doi.org/10.3390/gels8090568, 1-31.
Navarro-Tarazaga, M., et al., "Effect of Plasticizer Type and Amount on Hydroxypropyl Methylcellulose-Beeswax Edible Film Properties and Postharvest Quality of Coated Plums", J. Agric. Food Chem., vol. 56, 9502-9509 (2008), 10.1021/jf801708k.
Nechyporchuk, O., et al., "Production of Cellulose Nanofibrils: A Review of Recent Advances", Ind. Crops and Products, vol. 93, 2-25 (2016) http://dx.doi.org/10.1016/j.indcrop.2016.02.016.
Neibolts, N., et al., "Needle-Free Electrospinning of Nanofibrillated Cellulose and Graphene Nanoplatelets Based Sustainable Poly (Butylene Succinate) Nanofibers", Mat. Today Chem., vol. 17, 100301, 1-8 (2020).
Nelson, K., "Overview and Update of GranBio Nanocellulose Technology and Markets", Presentation—BDC 2020 Webinar Series, 1-33.
Nichols, G., et al., "A Review of the Terms Agglomerate and Aggregate with a Recommendation for Nomenclature Used in Powder and Particle Characterization", J. Pharmaceut. Sci., vol. 91, No. 10, 2103-2109 (2002).
Niinivaara, E., et al., "Bottom-Up Assembly of Nanocellulose Structures", Carbohyd. Polymers, (2020) doi: https://doi.org/10.1016/j.carbpol.2020.116664.
Osong, S., et al., "Processing of Wood-Based Microfibrillated Cellulose and Nanofibrillated Cellulose, and Applications Relating to Papermaking: A Review", Cellulose, 1-31 (2015), DOI 10.1007/s10570-015-0798-5.
Owonubi, S., et al., "Non-Woody Biomass as Sources of Nanocellulose Particles: A Review of Extraction Procedures", Front. Energy Res., 1-29 (2021) https://doi.org/10.3389/fenrg.2021.608825.
Pasaoglu, M., et al., "Substitution of Petroleum-Based Polymeric Materials Used in the Electrospinning Process with Nanocellulose: A Review and Future Outlook", Chemosphere, vol. 269, 128710, 1-14 (2020), https://doi.org/10.1016/j.chemosphere.2020.128710.
Pellis, A. et al., "Renewable Polymers and Plastics: Performance Beyond the Green", New Biotechnol., vol. 60, 1-53 (2021) https://doi.org/10.1016/j.nbt.2020.10.003.
Peng, Y., et al., "Drying Cellulose Nanofibrils: In Search of a Suitable Method", Cellulose, vol. 19, 91-102 (2012) DOI 10.1007/s10570-011-9630-z.
Peng, Y., et al., "Influence of Drying Method on the Material Properties of Nanocellulose I: Thermostability and Crystallinity", Cellulose, 1-14 (2013) DOI 10.10071s10570-013-0019-z.
Peng, Y., et al., "Spray-Drying Cellulose Nanofibrils: Effect of Drying Process Parameters on Particle Morphology and Size Distribution", Wood and Fiber Sci., 44(4), 448-461 (2012).
Ponni, R., et al., "Proposed Nano-Scale Coalescence of Cellulose in Chemical Pulp Fibers During Technical Treatments", BioResources, 7(4), 6077-6108 (2012).
Qin, C., et al., "MFC/NFC-Based Foam/Aerogel for Production of Porous Materials: Preparation, Properties and Applications", Materials, vol. 13, 5568, 1-21 (2020), doi:10.3390/ma13235568.
Rackaitis, M., et al., "Water-Soluble Polymers with Tunable Termperature Sensitivity: Solution Behavior", J. Polym. Sci. Part B: Polym. Phys., vol. 40, 2339-2342 (2002).
Raghav, N., et al., "Nanocellulose: A Mini-Review on Types and Use in Drug Delivery Systems", Carbohyd. Polymer Technol. Appl., 2, 1-10 (2020) https://doi.org/10.1016/j.carpta.2020.100031.
Rai, S., et al., "Environment-Friendly Nanocellulose-Indigo Dyeing of Textiles", Royal Soc. Chem., 2021, DOI: 10.1039/d1gc02043a.
Rallini, M., et al., "Nanofillers in Polymers", Modification of Polymer Properties, 47-86 (2017).
Rhodes, C., "Plastic Pollution and Potential Solutions", Sci. Progress, 101(3), 207-260 (2018), https://doi.org/10.3184/003685018X15294876706211.
Rhodes, C., "Solving the Plastic Problem: From Cradle to Grave, to Reincarnation", Sci. Progress, vol. 102(3), 218-248 (2019) https://journals.sagepub.com/doi/10.1177/0036850419867204.
Riekki, A., "Oil and Grease Resistant Paper-Board—Factors Affecting Barrier Properties and an Evaluation of the Test Methods", Tampere Univ., Faculty of Eng. and Nat. Sci., Master's Thesis, 1-83 (2019).
Rolsky, C., et al., "Degradation of Polyvinyl Alcohol in US Wastewater Treatment Plants and Subsequent Nationwide Emission Estimate", Int. J. Env. Res. Public Health, vol. 18, No. 6027, 1-15, doi.org/10.3390/ijerph18116027, (2021).
Rosenboom, J., et al., "Bioplastics for a Circular Economy", Nature Reviews Materials, vol. 7, 117-137 (2022).
Saito, T., et al., "Cellulose Nanofibers Prepared by TEMPO-Mediated Oxidation of Native Cellulose", Biomacromolecules, vol. 8, 2485-2491 (2007).
Sarr, M., et al., "Study on the Improvement of Interfacial Strength Between Glass Fiber and Matrix Resin by Grafting Cellulose Nanofibers", Compos. Sci. Technol., vol. 211, 108853, 1-12 (2021), https://doi.org/10.1016/j.compscitech.2021.108853.
Sehaqui, H., et al., "Stretchable and Strong Cellulose Nanopaper Structures Based on Polymer-Coated Nanofiber Networks: An Alternative to Nonwoven Porous Membranes from Electrospinning", Biomacromol., vol. 13, 3661-3667 (2012), dx.doi.org/10.1021/bm301105s.
Sharma, A., et al., "Commercial Application of Cellulose Nano-Composites—A Review", Biotech. Reports, e00316, 1-18 (2019), https://doi.org/10.1016/j.btre.2019.e00316.
Sheikh, A., et al., Materials Horizons, vol. 3, No. 1, Jan. 22, 2018, 1-11, DOI: 10.1039/C7MH00823F.
Sinquefield, S., et al., "Nanocellulose Dewatering and Drying: Current State and Future Perspectives", ACS Sust. Chem. Eng., vol. 8, 9601-9615 (2020), https://dx.doi.org/10.1021/acssuschemeng.0c01797.
Soane, D., "Advanced Polymer Composites", Slide Deck, 1-5.
Solhi, L., et al., "Understanding Nanocellulose-Water Interactions: Turning a Detriment into an Asset", Chem. Rev., vol. 123, 1925-2015 (2023), https://doi.org/10.1021/acs.chemrev.2c00611.
Svending, P., "Nanocellulose, Threat or Opportunity?", FiberLean Technologies, Presentation, London, 1-25 (2016).
Tantra, R., et al., "Dispersion Stability of Nanoparticles in Ecotoxicological Investigations: The Need for Adequate Measurement Tools", J. Nanopart. Res., 1-16 (2011), DOI 10.1007/s11051-011-0298-y.

(56) References Cited

OTHER PUBLICATIONS

Tayeb, A., et al., "Cellulose Nanomaterials—Binding Properties and Applications: A Review", Molecules, vol. 10, 1-32 (2018), doi:10.3390/molecules23102684.

Tomishige, K., et al., "Selective Transformation of Hemicellulose (Xylan) into n-Pentane, Pentanols or Xylitol over a Rhenium-Modified Iridium Catalyst Combined with Acids", Green Chem., vol. 18, 165-175 (2016) DOI: 10.1039/c5gc02183a.

Tsiopsias, C., et al., "On Polymer-Polymer Miscibility and Cellulose Ester Blends: A Case Study", Thermochimica Acta, vol. 714, 179265, 1-13 (2022), https://doi.org/10.1016/j.tca.2022.179265.

Tyagi, P., et al., "Nanocellulose-Based Multilayer Barrier Coatings for Gas, Oil, and Grease Resistance", Carbohydrate Polymers, 1-31 (2018), https://doi.org/10.1016/j.carbpol.2018.10.114.

Vieira, M., et al., "Natural-Based Plasticizers and Biopolymer Films: A Review", Europ. Polymer J., vol. 47, 254-263 (2010), doi:10.1016/j.eurpolymj.2010.12.011.

Vijayendra, S., et al., "Film Forming Microbial Biopolymers for Commercial Applications—A Review", Crit. Rev. Biotechnol., 1-20 (2013) DOI: 10.3109/07388551.2013.798254.

Wang, W., et al., "Improving Moisture Barrier Properties of Paper Sheets by Cellulose Stearoyl Ester-Based Coatings", Carbohydrate Polymers, 1-23 (2020), https://doi.org/10.1016/j.carbpol.2020.115924.

Wang, Y., et al., "Functional Nanomaterials through Esterification of Cellulose: A Review of Chemistry and Application", Cellulose, vol. 25, 3703-3731 (2018), https://doi.org/10.1007/s10570-018-1830-3.

Wei, D., et al., "Superhydrophobic Modification of Cellulose and Cotton Textiles: Mthodologies and Applications", J. Bioresources and Bioproducts, vol. 5, 1-15 (2020), https://doi.org/10.1016/j.jobab.2020.03.001.

Weidmann, The Leading Producer of Tailored Microfibrillated Cellulose "Corporate Slide Deck", Celova.

Willberg-Keyrilainen, et al., "Hydrophobization and Smoothing of Cellulose Nanofibril Films by Cellulose Ester Coatings", Carbohydrate Polymers, Apr. 25, 2017, 1-20, http://dx.doi.org/doi:10.1016/j.carbpol.2017.04.082.

Wojciechowska, P., et al., "Degradability of Organic-Inorganic Cellulose Acetate Butyrate Hybrids in Sea Water", Polish. J. Chem. Technol., vol. 13, No. 2, 29-34 (2011).

Wojciechowska, P., "The Effect of Concentration and Type of Plasticizer on the Mechanical Properties of Cellulose Acetate Butyrate Organic-Inorganic Hybrids", Recent Advances in Plasticizers, ISBN: 978-953-51-0363-9, Chapt. 8, 141-164 (2012).

Wozniak, A., et al., "Methods for Crosslinking and Stabilization of Chitosan Structures for Potential Medical Applications", J. Bioactive Compat. Polymers, vol. 37(3), 151-167 (2022), DOI: 10.1177/08839115221085738.

Xie, H., et al., "Recent Strategies in Preparation of Cellulose Nanocrystals and Cellulose Nanofibrils Derived from Raw Cellulose Materials", Int. J. Polymer Sci., vol. 2018, 1-26, Art. 7923068, (2018), https://doi.org/10.1155/2018/7923068.

Xie, Y., et al., "Silane Coupling Agents Used for Natural Fiber/Polymer Composites: A Review", Composites: Part A 41, 806-819 (2010), doi:10.1016/j.compositesa.2010.03.005.

Yadav, N., et al., "Degradable or Not? Cellulose Acetate as a Model for Complicated Interplay Between Structure, Environment and Degradation", Chemosphere, vol. 265 (2020), https://doi.org/10.1016/j.chemosphere.2020.128731.

Yang, Y., et al., "Phase Separation and Network Formation in Poly(Vinyl Methyl Ether)/Water Solutions", Polymer J., 33(5), 399-403 (2001).

Yaradoddi, J., et al., "Biodegradable Carboxymethyl Cellulose Based Material for Stustainable Packaging Application", Scientific Reports, 10:21960, 1-13 (2020), https://doi.org/10.1038/s41598-020-78912-z.

Yinxuan, L., "Research on Cellulose Film in Degradable Wet Garbage Bags", Polymer Sci peer Rev J., 4(1), 1-8 (2022), DOI: 10.31031/PSPRJ.2022.04.000580.

Zepic, V., et al., "Morphological, Thermal, and Structural Aspects of Dried and Redispersed Nanofibrillated Cellulose (NFC)", Holzforschung, 68(6), 657-667 (2014), DOI 10.1515/hf-2013-0132.

Zhang, H., et al., "Morphological Control and Interfacial Compatibilization of Fully Biobased PLA/ENR Blends via Partial Crosslinking ENR with Sebacic Acid", Ind. Crops Products, vol. 180, 114707, 1-12 (2022), https://doi.org/10.1016/j.indcrop.2022.114707.

Zhang, K., et al., "Understanding Plastic Degradation and Microplastic Formation in the Environment", Env. Pollution, vol. 274, 116554, 1-14 (2021), https://doi.org/10.1016/j.envpol.2021.116554.

Zhang, S., et al., "Reactive Superhydrophobic Paper from One-Step Spray-Coating of Cellulose-Based Derivative", Applied Surface Sci., vol. 497, (2019), https://doi.org/10.1016/j.apsusc.2019.143816.

Zimmerman, M., et al., "Drying Techniques Applied to Cellulose Nanofibers", J. Reinf. Plastics & Compos., 0(0), 1-16 (2016), DOI: 10.1177/0731684415626286.

Zimmerman, T., et al., "Applications of Nanofibrillated Cellulose in Polymer Composites", Presentation,. Int. Conference on Nanotech. for the Forest Products Industry, Espoo, Finnland 2010, 1-25.

Zuber, S., et al., "Effectiveness of Triacetin and Triethyl Citrate as Plasticizer in Polyvinyl Alcohol", Materials Today, Proc. 17, 560-567 (2019).

ARTICLES OF MANUFACTURE COMPRISING NANOCELLULOSE ELEMENTS

RELATED APPLICATIONS

This application is a continuation of application Ser. No. 18/588,964 filed Feb. 27, 2024, which is a continuation of application Ser. No. 18/123,476 filed Mar. 20, 2023 (now U.S. Pat. No. 11,932,829), which is a continuation of application Ser. No. 17/834,521 filed Jun. 7, 2022, which claims the benefit of U.S. Provisional Application No. 63/208,577 filed Jun. 9, 2021, U.S. Provisional Application No. 63/219,686 filed Jul. 8, 2021, and U.S. Provisional Application No. 63/309,730 filed Feb. 14, 2022. The entire contents of the above applications are incorporated by reference herein.

FIELD OF THE INVENTION

This application relates to nanocellulosic materials.

BACKGROUND OF THE INVENTION

Cellulose, the main building block for wood and plant fibers, is an abundant resource for the paper, textile, and chemical industries. It is a high molecular weight homopolymer of 1,4-linked β-D-glucopyranose units in which each unit is rotated 180° with respect to adjacent units. The monomeric glucopyranose units each contain three hydroxyl groups, which present themselves on alternating opposite sides of the polymer because of the rotational pattern of their linear arrangement within the polymer. The alternating orientation of the hydroxyl groups along the length of the cellulose molecule allows one strand of cellulose to form hydrogen bonds readily with adjacent strands of the polymer. These hydrogen bonds permit the formation of multistrand composites that are stable, strong, and tightly cohesive.

In biological systems, individual polymeric cellulose molecules form larger units with similar molecules. Biosynthesis within a plant can allow about thirty-six individual molecules to be bound together compactly, thereby forming the most basic building blocks of the plant's cell wall. These building blocks are called elementary fibrils (also termed microfibrils). The elementary fibrils, formed during the biosynthesis of cellulose in the biological entity, are about 5 nm in diameter and can be several micrometers in length. Each elementary fibril is a flexible elongated strand comprised of crystalline regions of cellulose interspersed with disordered amorphous domains of cellulose. The crystalline regions are segments of cellulose chains that have been rigidly stabilized by a strong intersecting network of hydrogen bonds; the amorphous regions, while still bound by hydrogen bonds, are more flexible. These elementary fibrils (microfibrils) are packed together in biological systems to form larger units called microfibrillated cellulose, which have diameters ranging from about 20-50 nm. In biosystems, the microfibrillated cellulose units are aggregated, linked via hemicellulosic moieties, and embedded in a pectin matrix to form the visible cellulose fibers found in plant cell walls.

The structures of elementary cellulose fibrils and microfibrillated cellulose permit two discrete cellulose morphologies to be extracted from the plant-derived cellulosic raw materials. Crystalline cellulose can be extracted in particulate form, yielding products that are termed cellulose nanocrystals or cellulose microcrystals, depending on the size of the particles. Cellulose can also be extracted as fibers, yielding products that are termed cellulose nanofibers or cellulose microfibers, depending on the size of the fibers. Cellulose crystals and cellulose micro/nano fibers are extracted by different techniques, yielding different morphologies with different properties. The two fibrous materials, cellulose nanofibers and cellulose microfibers, are extracted from plant matter by different techniques from each other, so that their morphologies and properties are different. Cellulose nanofibers and cellulose microfibers can be distinguished from each other based on their size and shape: cellulose nanofibers (CNF, also known as "nanofibrillated cellulose" or "NFCs") are much smaller in diameter than cellulose microfibers (CMF, also known as "microfibrillated cellulose" or "MFCs") and can be straight and rod-like, while CMF are larger in diameter, more flexible in appearance and can be irregular in shape. While the literature cites a range of dimensions for CNF and for CMF, CNF fibers are nanoscale (for example, having a diameter between 4-20 nm), while CMF can be much larger still: CMF fibers typically still have diameters in the nano-range, for example 20-100 nm or larger.

In more detail, CMF fibers are produced by mechanical treatment of cellulosic feedstock, with or without chemical or enzymatic pre-treatment. CMF fibers are elongated with a high aspect ratio, containing crystalline and amorphous regions like native cellulose, and capable of forming a three-dimensional network. The size distribution of CMF fibers in a fiber population is wide, with smaller, nanoscale fibers interspersed in the CMF network with larger fibers. By contrast, for CNF fibers, different processing methods are involved to produce populations of individual fibrils with a narrow size distribution within the population. The dimensions in the CNF material are more consistently nanoscale, as compared to CMF fiber populations. As used herein, all three species (crystalline cellulose, CNF, and CMF) shall be included in the umbrella term "nanocelluloses" or nanocellulose elements (NCEs).

Nanocellulose (NC) materials hold immense promise for commercial applications, thanks to their biodegradable nature, low density, abundant source materials, and high mechanical performance. However, although the nano-size geometry and hydrophilic nature of these cellulosic materials offer opportunities, these features also present challenges. A number of applications have been developed that exploit NC's geometry and hydrophilicity. As an example, certain nanocelluloses can be dry blended with inorganic powders, including plaster and cement, to deliver mechanical fortification to structures upon hydration and curing. However, because they are hydrophilic, NC materials require modification so that they can be used in hydrophobic environments. Even in hydrophilic environments, or within a composite that uses the NC as a hydrophilic component, satisfactory NC dispersion can be difficult, limiting the usefulness of NC elements in many applications. Furthermore, limitations imposed by NC drying and dispersion techniques limit the usefulness of these materials for commercial applications.

NCs are usually produced by a series of mechanical and/or chemical procedures performed in an aqueous medium, whereby the aqueous suspension loosens cellulose's interfibrillar hydrogen bonding to facilitate delamination, resulting in the formation of NC derivatives having more useful degrees of polymerization and crystallinity and having higher aspect ratios. Typically, the NC materials are dispersed in the aqueous medium at a low concentration (<5 wt %) because their high water-absorption capacity cause them to form a highly viscous suspensions even at low solid concentrations, due to the entangling of the high-aspect-ratio NC elements.

However, these aqueous suspensions of NCs are difficult to manage and expensive to transport. Therefore, drying technologies have been devised to convert the NC suspension into a dry powder form. However, drying the NC suspension using conventional techniques (for example, evaporating the water at high temperatures) promotes the formation of aggregates ("aggregation") due to the interaction of hydroxyl groups on the surface of the cellulose molecules, and the formation of hydrogen bonds. This aggregation process resulting from conventional drying, also called hornification, is characterized by irreversible or only partially reversible bonding between the hydroxyl groups on the NC particles or fibers.

Despite a decade-long series of academic and industrial efforts, success in low-cost and effective drying and redispersion has eluded NC producers. The twin challenges of (a) NC drying from the aqueous media in which the NC is suspended and (b) redispersion of the dried NC is caused by two factors: (1) the propensity of cellulose polymers to form hydrogen bonds with one another, adhering adjacent cellulosic elements into irreversible aggregates (i.e., an assemblage of particles durably attached to each other, resisting redispersion in a suspension); and (2) the huge surface area (per unit weight) associated with the size and morphology of the NCE, greatly exacerbating adhesion due to hydrogen bonding. If an aqueous slurry of NC is dried in a standard oven, a rigid, intimately entangled, brick-like mass is formed on the bottom of the drying vessel. This tight network of aggregated cellulosic elements cannot be easily scraped off the vessel, let alone be redispersed in water, even with intense mechanical agitation. Instead, attempts at redispersion result in large clumps of NC aggregates remaining in the redispersion medium even after hours of stirring. This resistance to redispersion prevents the use of the dried NC material in composite products (cement, concrete, paver, artificial stone, ceramic, plaster, mortar, joint compounds, and the like) in which a dry blend of the NC strengthening additive must be uniformly distributed throughout the composite.

This tendency towards aggregation and hornification and the subsequent resistance to redispersion has eluded a cost-efficient solution, thus foreclosing opportunities for using NC materials in a wide range of attractive applications. While various drying techniques, e.g., freeze drying, spray drying, supercritical fluid drying and atomization, have been investigated by researchers, they have at best yielded small samples of redispersed NC elements, using processes whose high cost, energy requirements, and need for specialized equipment preclude their widespread adoption.

There remains a need in the art, therefore, for commercial-scale drying techniques for NC materials that avoid the aggregation and hornification problems, so that solid masses of NC can be produced for later redispersion. There remains a further need in the art for such techniques that are suitable for commercial implementation, at low cost, without excessive energy requirements, and without need for specialized equipment.

SUMMARY OF THE INVENTION

Disclosed herein, in embodiments, are liquid formulations comprising a suspension of nanocellulose (NC) elements and a drying/dispersal additive, wherein the drying/dispersal additive is selected from the group consisting of temperature-responsive polymers, small molecule additives in volatile systems, and blocking agents. In embodiments, the nanocellulose elements are derived from lignocellulosic materials, which can comprise virgin biomass, and wherein the virgin biomass comprises specialty-purpose crops; in other embodiments, the lignocellulosic materials comprise waste materials. In embodiments, the NC elements comprise or consist essentially of crystalline cellulose, or cellulose nanofibers. In embodiments, the drying/dispersal additive is a temperature-responsive polymer, which can be a lower critical solution temperature (LCST) polymer or a short-chain oligomer derived from a LCST polymer. The LCST polymer can be selected from the group consisting of methyl cellulose, hydroxylethyl cellulose, hydroxypropyl cellulose, hydroxypropylmethyl cellulose, ethylhydroxyethyl cellulose, polyvinylcaprolactam, poly(methyl vinyl ether), poly (N-isopropylacrylamide), poly(N,N-diethylacrylamide), poly(ethylene oxide) and poly(propylene oxide) block copolymer, and elastin poly(pentapeptide). In embodiments, the drying/dispersal additive is a small molecule additive in a volatile system, which can be non-ionic or cationic, and which can be biodegradable. The small molecule additive can be selected from the group consisting of tri(propylene glycol)butyl ether, di(propylene glycol) propyl ether, propylene glycol butyl ether, propylene glycol propyl ether, ethylene glycol monobutyl ether, propylene glycol monomethyl ether acetate, propylene glycol diacetate, ethylene glycol diacetate, benzyl alcohol, 1-heptanol, and 1-hexanol. The small molecule additive can be selected from the group consisting of ethylene diamine, diethylene triamine, tetraethylene pentaamine, 1,3-pentane diamine, piperazine, 1,2-cyclohexane diamine, aniline, pyridine, and piperazine. In embodiments, the drying/dispersal additive is a blocking agent. The blocking agent can be a non-volatile chemical additive, which can be a purine or a pyrimidine. In embodiments, the non-volatile chemical additive is a purine, and the purine is a xanthine or a xanthine derivative. In embodiments, the blocking agent is a humectant, which can be selected from the group consisting of glycerin, caprylyl glycol, ethylhexylglycerin, tribehenin, hydrolyzed soy protein, propylene glycol, methyl gluceth-20, phenyl trimethicone, hyaluronic acid, sorbitol and gelatin. In embodiments, the blocking agent can be a fatty acid. In embodiments, the blocking agent comprises nanoscale particles. In embodiments, the liquid formulation can further comprise an adjuvant.

Also disclosed herein, in embodiments, are methods of processing cellulosic feedstock to form a redispersible, dried NC-containing material comprising NC elements, comprising mechanically defibrillating the cellulosic feedstock, thereby forming an initial nanocellulose suspension comprising the NC elements; treating the cellulosic feedstock with a drying/dispersal additive before or after the step of mechanically defibrillating the cellulosic feedstock to form a treated nanocellulose suspension comprising NC elements; and drying the treated nanocellulose suspension to form the redispersible, dried NC material comprising NC elements. The methods can further comprise a step of chemically pretreating the cellulosic feedstock either before or after the step of mechanically defibrillating the cellulosic feedstock, and the step of chemical pretreating can be performed using a pretreatment agent selected from the group consisting of enzymes, alkaline solutions, acid solutions, ionic liquids, short-chain amines, and positive oligomeric species. In embodiments, the pretreatment agent is selected from the group consisting of ethylenediamine, o-phenylenediamine, diethylenetriamine, tetraethylenepentamine, 1,3-diaminopentane, ethanolamine, triethynolamine, melamine, and EDTA. In embodiments, the methods further comprise a step of treating the cellulosic feedstock with a chelating agent before or after the step of mechanically defibrillating the cellulosic feedstock. In embodiments, the methods further comprise adding a second drying/dispersal additive to the cellulosic feedstock before, after, or simultaneously with the step of treating the cellulosic feedstock with the drying/dispersal additive.

In addition, a dried NC-containing material is disclosed herein that is produced by the methods described above. Further disclosed herein are methods of producing a formulation comprising suspended NC elements in a fluid medium, comprising providing the fluid medium, adding the redispersible, dried NC material described above to the fluid medium, and mixing the redispersible, dried NC material in the fluid medium, thereby suspending the NC elements in the fluid medium. In embodiments, the fluid medium is an aqueous fluid. Also disclosed herein are formulations comprising NC elements redispersed in a fluid medium produced by the methods described above.

Disclosed herein, in embodiments, are methods of producing a redispersible, dried NC-containing material with nanocellulose elements embedded therein, comprising providing the liquid formulation described herein, wherein the liquid formulation comprises nanocellulose elements and wherein the liquid formulation comprises a drying/dispersal additive; and drying the liquid formulation to form a dried NC-containing material with nanocellulose elements embedded within, wherein the redispersibility of the dried NC-containing material is greater than that of a dried control material prepared by drying a control suspension of nanocellulose elements in a liquid medium, wherein the control suspension lacks a drying/dispersal additive. The method can further comprise adding a pretreatment agent to the liquid formulation before the step of drying the liquid formulation; the pretreatment agent can be added before or simultaneous with addition of the drying/dispersal additive. In embodiments, the pretreatment agent is a chemical pretreatment, which can be selected from the group consisting of ethylene diamine, o-phenylenediamine, diethylenetriamine, tetraethylenepentamine, 1,3-diaminopentane, ethanolamine, triethynolamine, melamine, and EDTA. The chemical pretreatment can be a chelating agent. Further disclosed is a redispersible, dried, NC-containing material with nanocellulose elements embedded therein that is produced by the methods disclosed above. In embodiments, the nanocellulose elements are formed as a matrix, which can be a support for or a container for an active agent. Advantageously, the matrix can act as a container, and the container can be foamed. In embodiments, the matrix can be shaped as a formed article. In other embodiments, the matrix can be formed as a film, and the film can envelope the active agent. In embodiments, the formed article is adapted for disruption by a physical, chemical, or biological mechanism, wherein the disruption permits release of the active agent. In embodiments, the formed article comprises a first matrix acting as a support for the active agent, wherein the first matrix is formed as a sheet. In other embodiments, the formed article comprises a first matrix formed as a sheet and a second matrix formed as a sheet, with the active agent disposed between the first matrix and the second matrix, and the active agent can be enclosed between the first matrix and the second matrix. In embodiments, the active agent is selected from the group consisting of laundry products, soaps, detergents, surfactants, bleaches, enzymes, hair hold products, pigments, coloring agents, odor-related agents, emollients, cosmetics, pharmaceutical products, medical products, and agricultural active ingredients. In embodiments, the matrix further comprises filler particles, which can act as pore closure materials. In embodiments, the matrix has abrasive properties. In embodiments, the NC-containing material further comprises a barrier-producing material, which can be deployed as a coating on an upper or lower aspect (e.g., on the top or bottom) of the matrix, or which can be mixed into the matrix. In embodiments, the barrier producing material imparts oil and grease resistant properties to the NC-containing material, or imparts water resistant or water-vapor resistant properties to the NC-containing material. In embodiments, the barrier-producing material comprises a biopolymer.

Also disclosed herein, in embodiments, are methods of redispersing nanocellulose elements, comprising providing the redispersible, dried, NC-containing material described above, and adding a redispersing fluid to the dried NC-containing material, thereby redispersing the NCEs embedded in the redispersible, dried NC-containing material. The redispersing fluid can be an aqueous fluid. Further disclosed herein are redispersed NC-containing formulation comprising NC elements suspended in a redispersing fluid, wherein the redispersed NC formulation has been produced by the methods described above. In embodiments, the formulation can be foamed. In embodiments, the formulation further comprises an active agent attached to the NC elements or embedded in a matrix formed from the NC elements. In embodiments, the active agent can be a skin-treating substance, or a pharmaceutical or nutraceutical product, or a cosmetic product, or an odor-related active agent, or an agricultural active ingredient. Also described herein are methods of manufacturing a formed article, comprising drying the formulation described above into a selected shape, wherein the selected shape when dried produces the formed article. In addition, methods are disclosed herein for treating a surface, comprising applying the formulation described above to the surface and allowing the formulation to dry. In embodiments, the surface is a hair shaft or a skin surface. In embodiments, methods are disclosed herein for treating a skin disorder or skin condition, comprising applying the formulation described above to a selected area of skin in need of treatment. Methods are also disclosed herein for treating an agricultural product, comprising applying the formulation described above to the agricultural product.

Further disclosed herein, in embodiments, are methods of producing a composite matrix, comprising providing an existing matrix composition, and incorporating a population of additive NCEs into the existing matrix. The existing matrix composition can comprise or consist essentially of organic materials, which can be pulp or pulp-based material. In embodiments, the existing matrix composition is coated with or impregnated with the additive NCEs. Also disclosed herein are composite materials prepared by the foregoing methods. In embodiments, the existing matrix is a hydrophobic matrix, and the additive NCEs have been hydrophobized for use in the hydrophobic matrix. In embodiments, the existing matrix comprises a biodegradable polymer, which can be a natural polymeric material. In embodiments, at least a portion of the additive NCEs act as fillers or act as pore-closers in the existing matrix. In embodiments, the composite material further comprises a secondary additive, which can be a plasticizer or a hydrophobic cellulose additive. In embodiments, the composite material exhibits a specialized property, which can be is selected from the group consisting of a mechanical property, a barrier property, and an adscititious property. In embodiments, the specialized property is a mechanical property, which can be a reinforcement of a mechanical characteristic of the existing matrix. In embodiments, the specialized property is a barrier property, which can be an oleophobic barrier property, a hydrophobic barrier property, or both. In embodiments, the specialized property is an adscititious property, which can be a conductive property. In such embodiments, the population of additive NCEs can include a subpopulation of NCEs having conductive properties, and the conductive properties of the subpopulation can be produced in the subpopulation via the silver mirror reaction. In embodiments, the composite material can be a foamed article, which can comprise cellulose microfibers within the population of additive NCEs; in embodiments, the foamed article can comprise a barrier-producing material. Further disclosed herein are articles of manufacture comprising the composite materials disclosed above. In embodiments, the article of manufacture is selected from the group consisting of recreational equipment articles, athletic shoes, architectural paint products, construction materials, durable inks, and 3D printing materials. In embodiments, the article of manufacture can comprise the composite material disclosed above, wherein the composite material exhibits a specialized property. Such articles of manufacture can be formed as drinking straws, films, sheets, or fibers or non-woven fabrics; such fibers or non-woven fabrics can exhibit optimized properties, and they can be formed into an artificial leather.

DETAILED DESCRIPTION OF THE INVENTION

1. Constituents for Redispersible Nanocellular Materials

It is understood that NC materials suitable for treatment with the systems and methods disclosed herein can be derived from all types of cellulosic raw materials, in particular plant-derived cellulosic raw materials, which can also be termed lignocellulosic materials. Lignocellulosic materials are formed of cellulose polymers as described above bound with varying amounts of lignin. Lignocellulosic materials can include virgin biomass, as is found naturally occurring plants like trees, bushes, and grass. Lignocellulosic materials can include waste materials from consumption or from industries such as agriculture (e.g., corn stover and corncobs, sugarcane bagasse, straw, oil palm empty fruit bunch, pineapple leaf, apple stem, coir fiber, mulberry bark, rice hulls, bean hulls, soybean hulls (or "soyhulls"), cotton linters, blue agave waste, North African glass, banana pseudo stem residue, groundnut shells, pistachio nut shells, grape pomace, shea nut shell, passion fruit peels, fique fiber waste, sago seed shells, kelp waste, juncus plant stems, and the like), or forestry (saw mill and paper mill discards). Lignocellulosic materials can include specialty-purpose crops such as switchgrass and elephant grass cultivated for uses such as biofuels, capable of multiple harvests. Plants having use as lignocellulosic materials can be woody (such as trees, with firm stems, and with multiyear growth cycles) or non-woody, having weak stems and annual or limited multiyear growth cycles. Non-woody plants are particularly advantageous, typically possessing low amounts of lignin relative to the amount of cellulose they contain. As would be understood by those of skill in the art, different techniques are available for processing the various lignocellulosic materials to extract NC materials therefrom.

Disclosed herein, in embodiments, are additives that can be used for inhibiting or disrupting the hydrogen bonding of NC materials at elevated temperatures (for example, during drying), while retaining high intrinsic hydrophilicity, thus allowing facile redispersion in aqueous media. The formulations and methods disclosed herein include several different categories of additives (termed "drying/dispersal additives"): (1) certain temperature-responsive polymers that can introduce spacing between NC particles or fibers (collectively, "NC elements") during drying, thus preventing their clumping; (2) certain volatile small molecules that can create space between NC elements during drying; and (3) certain nonvolatile small or large molecules that hinder hydrogen bonding between or among NC elements during drying. All of these materials act to disrupt hydrogen bonding at elevated temperatures or under other circumstances, while creating gaps between or among the NC elements with further drying that will permit subsequent redispersion.

As used herein, the term "drying" for an initial suspension of NC elements (termed the "initial NC suspension," understood to be the suspension containing the NC elements that is initially produced during the defibrillation processes, as exemplified in the description that follows) refers to the application of heat and/or any other dewatering technology to the initial NC suspension that results in a decrease in the water content of the initial NC suspension so that the initial NC suspension is converted to a solid or semi-solid material comprising the NC elements that were present in the initial NC suspension. This dried solid or semi-solid material can be referred to as the "dried NC material." As used herein, the term "redispersion" refers to a process by which the dried NC material is suspended in a fluid medium (whether aqueous or non-aqueous) so that there is a substantially complete dissolution of the dried NC material (whether semi-solid or solid) into its component NC elements. In embodiments, aqueous resuspending fluids can be used; in other embodiments, non-aqueous resuspending fluids can be used, such as fluids having hydrophobic properties or amphiphilic properties. In embodiments, redispersion results in a suspension of the NC elements so that they are formed as individual NC elements or coalescences of individual NC elements (either, referred to herein as a "resuspended particles") wherein such resuspended particles have an aspect ratio of greater than 10. In embodiments, the resuspended particles have an aspect ratio between about 10 and about 300, or between about 10 and about 200. In embodiments, the resuspended particles have an aspect ratio between about 50 and about 150. In embodiments, the resuspended particles have an aspect ratio between about 25 and about 75. In other embodiments, the resuspended particles have an aspect ratio between about 75 and about 125.

While certain additives (for example, certain LCST polymers, as described below) are suitable for use as single agents for facilitating drying and redispersion, other additives lend themselves for use as adjuvants in combination with a main drying/dispersal additive, either administered into the initial NC suspension simultaneously with the main additive, or as pre-treatment to the initial NC suspension or any precursor thereof before adding the main additive, or as a post-treatment to the initial NC suspension following the addition of the main drying/dispersal additive. Drying/dispersal additives comprise, without limitation, temperature-responsive polymers, small molecule additives in volatile systems, and blocking agents. Main drying/dispersal additives and adjuvant additives that are used in combination with a source of NC elements to produce the liquid formulations and derivative redispersible dried materials of the present invention are termed, collectively, "primary additives."

a. Temperature-Responsive Polymers

In embodiments, certain temperature-responsive polymers can be employed to create space between the NC elements during drying, thereby preventing the NC elements from aggregating during the drying process. Temperature-responsive polymers especially suitable for this purpose are those that exhibit a phenomenon known as LCST (lower critical solution temperature) phase behavior. It is understood that certain LCST polymers are hydrophilic below their LCST transition temperature and become reversibly hydrophobic above their LCST transition temperatures. In other words, below the LCST point, the polymer shows high affinity towards water, consistent with its intrinsic molecular hydrophilicity. However, above the LCST point, the polymer repels water and shuns hydrogen bonding. This is evidenced by the observed thermogelation of polymer solutions above this transition temperature. As the polymeric or oligomeric LCST additive self-assembles on the surface of the NC elements (in the form of mono-layer or a few molecular layers), drying of NC elements are affected so that their ultimate redispersion is facilitated.

In more detail, the LCST polymer can be added to the initial NC suspension at a temperature below the LCST polymer's transition temperature. As water evaporates from the initial NC suspension during drying, its temperature rises and approaches the boiling point of water, coming to exceed the LCST polymer's transition temperature, at which point the LCST polymer loses its hydrophilic character and becomes hydrophobic. When it becomes hydrophobic, the LCST polymer interferes with the hydrogen bonds that are forming between the NC elements. The hydrophobic nature of the LCST polymer now dictates aggregation or disaggregation of the NC elements, instead of these processes being driven by the interaction of the cellulosic units of the NC elements.

In embodiments, selected LCST polymers can markedly or completely hinder the dense aggregation of NC elements upon drying. In embodiments, the ability of selected LCST polymers to disrupt aggregation of NC elements is independent of equipment selection and manner of drying. For example, the suspension containing the LCST polymer and the NC elements can be left quiescent during drying. A wide range of drying temperatures and pressures can be applied to the initial NC suspension in the presence of selected LCST polymers to accomplish aggregate-free drying. Dried NC materials produced using selected LCST polymers as described herein can be readily redispersed in water with gentle agitation or stirring, with minimal or no clotting or residual aggregations identified in the redispersed suspension. These features give rise to wide latitude in processing parameters.

In embodiments, the list below offers examples of LCST polymers and their analog short-chain oligomers that can be used to prevent aggregation and facilitate redispersion of NC elements.

- Methyl cellulose
- Hydroxyethyl cellulose
- Hydroxypropyl cellulose
- Hydroxypropylmethyl cellulose
- Ethylhydroxyethyl cellulose
- Polyvinylcaprolactam
- Poly(methyl vinyl ether)
- Poly(N-isopropylacrylamide)
- Poly(N,N-diethylacrylamide)
- Block copolymer of poly(ethylene oxide) and poly(propylene oxide)
- Poly(pentapeptide) of elastin Note that thermo-gelation temperature of the cellulose derivatives listed above depends on the type and degree of substitution and is tunable by structural design. Advantageously, a selected LCST polymer for use as a drying/dispersion additive can have a transition temperature that is greater than the ambient temperature (for example, >25° C.), so that the polymer remains in solution until the drying step commences.

b. Volatile Small-Molecule Additive Systems

In embodiments, volatile systems comprising small molecule additives can be employed to create space between the NC elements during drying to prevent the NC elements from aggregating during the drying process, either alone or in combination with other additives. The selected small molecule additives for use with volatile systems are miscible with water and have a boiling point higher than that of the co-existing water. The small molecule additive useful in a volatile system is further characterized by its greatly lower hydrogen-bonding tendency compared to water. As the additive-loaded volatile system containing the NC and the selected small molecules undergoes drying, water molecules evaporate preferentially, leaving the small molecule additive behind due to its higher boiling point and thereby increasing the concentration of the additive in the solution that remains between adjacent NC elements. In embodiments, the molecular segments of the volatile small molecule additives comprise both polar and non-polar functionalities. Not being bound by theory, it is envisioned that the polar segments are attracted by the cellulosic hydroxy groups while the non-polar segments simultaneously interfere with hydroxy-hydroxy interactions, thus reducing adherence between and among the NC elements. Then, as the temperature in the system rises, the additive evaporates, leaving behind the NC elements surrounded by air. The resulting dried material, containing NC elements that are separated from each other by air, can be readily re-dispersed without the formation of observable clumps/clots or concentration variations. The redispersed suspension comprises resuspended NC particles that are uniform in distribution within the suspension, wherein the NC elements retain their nano-size characteristics and can achieve redispersion with only very mild agitation/stirring.

In embodiments, the lists below offer examples of small molecule additives that can be used in the aforesaid volatile systems to prevent aggregation and facilitate redispersion of NC elements. Exemplary additives can be divided into two categories: non-ionic and cationic compounds.

Non-ionic candidates can include, without limitation:
- Tri(propylene glycol) butyl ether (TPnB)
- Di(propylene glycol) propyl ether (DPnP)
- Propylene glycol butyl ether (PnB)
- Propylene glycol propyl ether (PnP)
- Ethylene glycol monobutyl ether
- Propylene glycol monomethyl ether acetate
- Propylene glycol diacetate
- Ethylene glycol diacetate
- Benzyl alcohol
- 1-Heptanol
- 1-Hexanol Cationic candidates can include, without limitation:
- Ethylene diamine
- Diethylene triamine
- Tetraethylene pentaamine
- 1,3-Pentane diamine Piperazine
1,2-Cyclohexane diamine
Aniline
Pyridine
Piperazine In embodiments, the small molecule additives can evaporate completely from the initial NC suspension, just leaving behind the NC elements without additive residue. However, in other embodiments, trace amounts of the small molecule additives can remain. For example, with certain cationic additives, their cationic groups can adhere to cellulose molecules, so that trace amounts of the additive remain adherent to the cellulose after complete drying. For most industrial applications, the trace residues of these additives do not pose a health or environmental problem. However, in embodiments, a biodegradable cationic small molecule such as 1,3-pentane diamine is advantageous.

c. Blocking Agents

In embodiments, non-volatile small or large molecule additives can be employed themselves, apart from volatile systems as described above, to hinder hydrogen bonding and/or to create space between the NC elements during drying, thereby blocking interactions between the NC elements and thus preventing the NC elements from aggregating during the drying process. In embodiments, surface functionalized nanoscale particles can be employed in the same manner. Such non-volatile small or large molecule additives and nanoscale particles carrying out this blocking function are referred to herein as blocking agents or blockers As used herein, the term "blocking agent" or "blocker" includes any non-volatile chemical additive or nanoscale particulate material that itself hinders hydrogen bonding or creates spaces among NC elements, whether the substance is interposed between or among NC elements, or whether the substance offers temporary competitive binding sites for the NC elements, or otherwise. As an example, caffeine and other xanthine derivatives are small-molecule blockers that can be used advantageously to facilitate isolation and re-dispersion of NC elements. Not being bound by theory, it is envisioned that the aromatic nitrogen atoms in certain purines (such as caffeine and other xanthines or xanthine derivatives) and pyrimidines can become hydrogen-bonded with the hydroxy groups of the cellulose, presenting a flat, relatively non-polar, and molecularly-lubricating and water-screening outer surface, thus hindering adhesion between and among NC elements. Advantageously, caffeine, and other xanthines and xanthine derivatives can typically be used in quantities that do not present health or environmental problems even when used in sufficient dosages to facilitate NC dispersion.

As another example, certain humectant substances can be employed as blocker molecules. Humectants possess multiple hydrophilic sites (hydroxyls, esters, and ammonium groups) that can form hydrogen bonds with the surface of the NC elements, thus screening the interaction of these elements with each other via hydrogen bonding, and thereby impairing aggregation. Moreover, these hygroscopic substances are biocompatible and are already widely used in the pharmaceutical, cosmetic, and food industries. Exemplary short and long humectant candidates include but are not limited to: glycerin, caprylyl glycol, ethylhexylglycerin, tribehenin, hydrolyzed soy protein, propylene glycol, methyl gluceth-20, phenyl trimethicone, hyaluronic acid, sorbitol and gelatin.

As another example, fatty acids can be employed as blockers as well. Fatty acids contain hydrophilic sites and a hydrophobic tail. The hydrophilic site can form hydrogen bonds with the surface of NC elements, thus screening the interaction of these elements with each other via hydrogen bonding, and thereby impairing aggregation. Advantageously, fatty acids can be selected that do not contain so many hydrophilic sites that much hydrogen bonding will occur between fibers and the blockers. In embodiments wherein too many hydrogen sites may cause aggregation, the hydrophobic tail of the fatty acid blockers can act to physically prevent aggregation of NC elements by preventing or interfering with hydrogen bonding. In embodiments, the blocking agent can be a fatty acid, such as stearic acid, palmitic acid, myristic acid, lauric acid, capric acid, caprylic acid, caproic acid, and the like. For dispersion purposes, a water-soluble fatty acid may be preferable.

2. Additional Processing Options

It is understood that the drying/dispersal additives disclosed herein can be introduced into a NC-containing suspension individually or in combination to improve the drying process for the NC and to facilitate its redispersion. Drying/dispersal additives can also be used in combination with other agents that enhance their efficacy, even if those other agents are not effective as drying/dispersal additives when used alone; such agents, used in combination with the drying/dispersal additives to enhance their efficacy, are termed "adjuvants." It is further understood that one or more of the drying/dispersal additives or adjuvants can act together in a synergistic manner. Moreover, combinations of the drying/dispersal additives can be introduced sequentially during the preparation of the initial NC suspension, and/or before, after, or during the processes that are employed to produce the initial NC suspension from a feedstock of cellulosic sources, with or without the addition of adjuvants. For example, non-polymeric additives can be added during the processes that are employed to produce the initial NC suspension from feedstock, but desirably are to be added after chemical pretreatment.

Processes for forming NC-containing suspensions (i.e., initial NC suspensions) suitable for treatment using the formulations and methods disclosed herein are familiar in the art. To form such a NC-containing suspension, cellulose sources can be processed using mechanical techniques and optional chemical treatments to extract the component cellulose nanomaterials and retain them as suspended in a liquid medium. The NC elements thus extracted form the initial NC suspension, which can be treated using the disclosed formulations and methods.

In more detail, mechanical treatments such as high-pressure homogenization, microfluidization, super-grinding, cryo-crushing, steam explosion, refining, and high-intensity ultrasonication are known in the art for disintegrating the cellulose source materials to yield their component NC elements; other mechanical techniques will be familiar to artisans in the field having ordinary skill. Such mechanical treatments can be termed forms of mechanical defibrillation. Mechanical treatments, however, require considerable amounts of energy. Therefore, in order to reduce energy consumption during the mechanical defibrillation processes, a variety of chemical and enzymatic strategies have been employed to pretreat the cellulose sources before their mechanical processing, such strategies being collectively termed "chemical pre-treatments" herein. In addition, chemical modification of the NC elements can be performed after mechanical defibrillation to alter their properties.

Drying/dispersal additives as disclosed herein can be used in the various suspensions of partially treated cellulose sources, instead of or in addition to being used to treat the primary NC suspension resulting from the extraction of the NC elements from the cellulose source feedstock. In exemplary embodiments, a single drying/dispersal additive can be used to treat a feedstock suspension of partially treated cellulose sources, for example a suspension of cellulose sources that has been pretreated chemically but have not yet been subjected to mechanical defibrillation. For example, a volatile additive can be used in this way. Volatile additives are typically formulated as non-viscous fluids that can be injected directly into the pulp feedstock suspension, for example after its chemical pretreatment and/or immediately before it undergoes mechanical defibrillation process (homogenizing, microfluidization, grinding, high intensity ultrasonication, and the like). In this manner, volatile moieties are intermingled between and among individual fibers as they detach from larger pulp (cellulose) strands, an architecture that is retained during mechanical defibrillation.

In another embodiment, a non-volatile additive or a temperature-responsive polymer such as a LCST polymer can be used to treat the partially-treated cellulose feedstock instead of or in addition to using a drying/dispersal additive to treat the initial NC suspension. Non-volatile additives, as well as LCST polymers, generally come as viscous fluids or powdered solids to be dissolved aqueous solutions. Due to their high viscosity, these components are desirably added after mechanical defibrillation, either by direct application/dissolution or by combining a concentrated solution of the additive with the NC suspension effluent.

In other embodiments, pretreatments with various pretreatment agents may be useful prior to adding the drying/dispersal formulations disclosed herein. For example, cellulose sources can be subjected to certain chemical pretreatments before mechanical defibrillation, as mentioned above. Chemical pretreatments such as enzymes, alkaline-acid solutions, and/or ionic liquids, for example, can break down lignin and hemicellulose in cellulose sources, while preserving cellulose moieties. These chemical pretreatments help reduce the energy consumption of subsequent mechanical processing, as described previously. Furthermore, chemical pretreatments can render the surface chemistry of the extracted NC elements more receptive to treatment with the drying/dispersal additives disclosed herein. It is known that the surface chemistry of NC elements varies, depending on both the raw source of the cellulosic material (e.g., softwood, hardwood, soy hulls, wheat straw, bagasse, sugar beet pulp, and the like) and the processing technique implemented (e.g., Kraft vs Sunburst). Moreover, additional chemical treatments such as carboxymethylation, oxidation, and sulfonation can be implemented during industrial processes to create permanent anionic charges on the NC surfaces. To optimize the surface chemistry of a population of NC elements for treatment with the drying/dispersal additives disclosed above, these elements can be pretreated with short amines or positive oligomeric species to mitigate ionic forces between the NC elements; such pretreatment can be carried out before or in conjunction with adding the drying/dispersal additives. Examples of such pre-treatment agents include: ethylene diamine, o-phenylenediamine, diethylenetriamine, tetraethylenepentamine, 1,3-diaminopentane, ethanolamine, triethynolamine, melamine, and EDTA; other pre-treatment agents will be familiar to those having ordinary skill in the art.

In certain embodiments, chelating agents such as EDTA or comparable chelating agents such as MGDA (methylglycinediacetic acid trisodium salt), GLDA (tetrasodium glutamate diacetate), GEDTA (EGTA) (ethylene glycol-bis(β-aminoethyl ether)-N,N,N',N'-tetraacetic acid), and the like, are useful as pre-treatments if a hard water source is employed to suspend the NC elements. In an embodiment, a LCST polymer can be selected as a drying/dispersal additive, to be used in a NC suspension after using or simultaneously with using EDTA to chelate the hard water cations. In embodiments, a chelating agent such as EDTA can be used to treat the initial NC suspension, thereby complexing divalent cations resident in the suspending fluid.

Other useful pre-treatments can be readily envisioned by those having ordinary skill in the art.

3. Exemplary Articles of Manufacture

In embodiments, nanocellulose elements (NCEs) prepared in accordance with the systems and methods disclosed herein can be incorporated into a wide range of articles of manufacture. NCEs offer significant advantages for forming commercial products.

In embodiments, these materials can be engineered to provide a matrix that supports other active agents in formulations or compositions; such materials advantageously provide vehicles having properties such as optical transparence and mechanical strength for carrying and delivering the active agents conveniently for their intended use. As used herein, the term "active agent" refers to any substance that produces a desired chemical, physical, or biological effect, wherein the substance is capable of producing a chemical, physical, or biological effect independent of its association with the NCE products (matrices, coatings, substances, fillers, etc.) as disclosed herein. Such active agents can be contained in (e.g., transported within, enveloped by, dispensed from, or otherwise directed to a designated site of activity by) the NCE-based products disclosed herein. As examples without limitation, active agents can include laundry products (e.g., substances such as laundry detergents, bleaches, enzymes, and fabric softeners), soaps, cosmetics, pharmaceutical products, agricultural active ingredients, and the like (certain of which are described in more detail below); such active agents can be supported by a NCE matrix, embedded in it, attached to it, or otherwise associated with it, wherein the matrix permits the active agent to be delivered to the site of activity for the active agent. In certain embodiments, a NCE-based matrix can support the inclusion of active agents having their own properties but that are intended to modify the intrinsic properties of the matrix itself, such as pigments, dyes or other colorizing agents to add or change color, fragrances, odor absorbers, disinfectants, and the like; such active agents can thereby become incorporated into an article of manufacture comprising the matrix, to impart their properties to the final formed article.

In other embodiments, materials comprising NCEs can be incorporated into non-NCE matrices to improve the properties of such non-NCE matrices, including, inter alia, improved strength and resiliency. As has been described above, notwithstanding the cheap, abundant, sustainable and biodegradable features of NCEs, their widespread adoption in articles of manufacture has been constrained by the drawbacks associated with the suspension of these particles:

once suspended, NCEs require transportation in substantial volumes of liquid; if the suspension dries, it undergoes irreversible hornification, which prevents the NCEs contained therein from becoming resuspended. The methods and compositions disclosed herein make NCEs resuspendable, and thus available for inclusion in a variety of products, examples of which are set forth in the present disclosure.

a. NCEs as Matrices: General Characteristics

Dispersed NCEs produced as disclosed herein can be formed into highly porous three-dimensional nanoscale networks capable of holding functional or active agents within their interstices, and capable of being engineered to optimize their own intrinsic properties with or without adding other ingredients. Such matrices can be formulated as solids, gels, liquids, and the like, to meet the specific product's needs. Moreover, the matrices, once created, can be shaped or molded into any convenient geometry, such as chips, strips, balls, cubes, sheets, etc., as required by the product category, to produce articles of manufacture. Once formed, a NCE matrix can be used as is, or can be redispersed in water or other aqueous redispersion fluids to form the final product.

In embodiments, an NCE-based matrix article of manufacture is intended to envelop, contain, enclose, support, or otherwise deliver active agents. In embodiments, the NCE-based matrix acts as a carrier for other active agents, with the active agents embedded within, attached to, or supported by the matrix structure; under such circumstances, the matrix can be termed a support for the active agent. In other embodiments, the NCE-based matrix encloses or envelopes the active agent, and acts as a container for the active agent. In either case, the matrix serves to convey the active agent to a site of its activity, and the matrix is engineered to deliver the active agent to the site of its activity. Articles of manufacture can be constructed comprising NCE-based matrices acting as supports, containers, or both. In embodiments such articles of manufacture can be adapted for disruption by physical, chemical, or biological mechanisms, thereby releasing the active agents they support or contain. Such articles of manufacture can be engineered to produce, for example, frangible or dissolvable or other properties permitting disruption (e.g., able to be digested by microorganisms or hydrolyzed by enzymes), so that they are adapted for delivery of the active agents they contain, for example upon encounter with mechanical force (e.g., tearing, squeezing, puncturing, and the like) or upon encounter with a chemical solvent such as an aqueous fluid or upon encounter with a destructive biological entity. The encounter of the article of manufacture with such physical, chemical, or biological mechanisms can impair the integrity of the article of manufacture sufficiently to permit it to deliver the active agent it contains or supports into/onto the area, surface, substance, etc., designated for the activity of the active agent.

In other embodiments, the structure of the NCE matrix itself provides the desired properties for the article of manufacture. A NCE matrix can be shaped to provide the structural and architectural features that a particular application requires. Under these circumstances, the NCE matrix produces the desired effects in a product by virtue of its mechanical or structural properties. In embodiments, the NCE matrix can incorporate secondary additives that impart other advantageous properties to the matrix itself, apart from the ability of the matrix as a carrier for active agents.

Examples of NCE matrices as carriers for active agents and as structural units or components are set forth below, to illustrate the principles of the invention.

i. NCE Matrices as Carriers: Product-Dispensing Vehicles

NCE matrices are suitable for use in a variety of product dispensing applications, and can readily serve as convenient vehicles for dispensing products that are embedded within the matrix. Without being bound by theory, it is understood that active agents can be introduced into NCE matrices so that they are infused into and reside within the interstices, or coat the matrix framework or both. A variety of advantageous properties can be imparted to an article manufactured from NCE matrices, by introducing secondary additives into the matrix that convey the desired properties. For example, specialized release paper can be prepared using silicone adhesives within the NCE matrix, so that less adhesive backing is required.

In embodiments, NCE matrices can serve as vehicles for active agents used in the household products and personal care industries. Because they can be dehydrated and redispersed, NCE compositions prepared in accordance with the methods disclosed herein can be used as vehicles for active agents such as detergents, bleaches, fabric softeners, soaps, fragrances, skin care items, cosmetics, and the like.

Once the desired NCE matrix suspension has been formed, including the active agents and other secondary additives disposed within, it can be dried for use as a formed article. A dried NCE suspension containing the desired active agents in the NCE interstices can be formed as a dried or gelatinized sheet, a chip, a ball, a cube, etc., that can then be rehydrated with resuspension and release of the active agent. These form factors enable convenient transportation and storage for the formulation without requiring a large fluid volume.

For example, a sheet can be formed using an NCE-based matrix to dispense products or active agents in a desired environment over a desired time period. Sheets can be formed from NCE-mased matrices that have detergent and/or other laundry agents (e.g., enzymes or bleach) disposed within the matrix interstices; this sheet can be delivered into a washing machine or dishwasher and allowed to come into contact with water, allowing the laundry agents(s) to be delivered and the NCE-based matrix to be ultimately dissolved with dispersal of the NCE components.

As another example, a redispersible dried chip, plaque, strip, or the like, can thus support a variety of active agents in a convenient, dry vehicle, allowing them to be released as a finished formulation with simple rehydration or redispersion. As an example, soap or shampoo chips can be produced from a NCE suspension containing the desired soap products by dehydrating the suspension to produce a solid composition. The lightweight, conveniently sized chip can be rehydrated with water by the consumer, to form a reconstituted, finished liquid formulation on an as-needed basis. In a commercial embodiment, a manufacturer can produce precisely measured chips for use with proprietary vessels of known volume, allowing the consumer simply to insert the chip and fill the vessel with the designated amount of water. In embodiments, a vessel for reconstituting the NCE-based composition can be reusable, thus permitting the manufacturer to avoid the use of plastic or glass containers for transporting, displaying, and storing household products or cosmetics. In other embodiments a vessel is not needed, and a chip of the NCE-based composition can be held in the hands while washing with water. Thus, reconstitution happens during the hand-washing process, which can be especially useful for traveling or in areas where water is not readily available.

While a flattened chip shape has been described as an exemplary embodiment, it is understood that the NCE-based composition can be formed in any desirable geometry, including but not limited to regular or irregular spheres, rectangles, cubes, cylinders, thick sheets, rolls, and the like, with the shape selected to provide an appealing form for customer utilization.

Examples of active agents usable within NCE-based matrices for household uses include bleaches, laundry detergents, and combinations thereof, dishwasher soap and dishwasher treatments, toilet bowl cleaners, and other industrial heavy-duty cleaning products such as oven cleaners, floor cleaners, and the like. These products can be formulated to incorporate other advantageous properties, such as sustained release. Analogous NCE-based products can be envisioned for other fields, such as medical products in which the active agent can be borne within the matrices of the NCE composition.

In embodiments, active agents such as are exemplified above can be embedded in sheets formed from NCE matrices to be delivered in clothes dryers, as substitutes for the familiar dryer sheets. Conventional dryer sheets are fibrous sheets, usually made from compressed polyester or cellulose fibers, that are coated in a thin, waxy layer of laundry products like fabric softeners, scents, static reducers, and the like. When used in a hot dryer, these laundry substances melt off the dryer sheet fibers and distribute evenly throughout the laundry load, applying all the benefits of the materials listed. However, the materials used in conventional dryer sheets can be petroleum-derived, and can resist biodegradation, leading to a buildup of these materials in landfills. As an alternative, NCEs can be used as the carrier matrix for the laundry products, replacing conventional nonwoven materials, providing an environmentally friendly, biodegradable alternative to conventional dryer sheets. In embodiments, NFCs, MFCs, or mixtures thereof can be used alone or in combination with other matrix materials such as pulp or pulp-based materials to make articles like the dryer sheets disclosed herein. Advantageously, use of a NCE matrix provides high strength and biodegradability, while forming a porous material that can act as a carrier for the active agents to be distributed within the dryer.

To this end, the formulations for NCE redispersion as disclosed herein can be modified to have higher concentrations of hydrophobic cellulose polymer (for example, including a hydrophobic cellulose polymer (e.g., methyl cellulose) in ranges from about 0% to about 10%) to create a strong network of fibers. In embodiments, the plasticizer should preferably be hydrophobic to protect the sheet from being saturated by water and weakened. Plasticizers such as the diesters and triesters of certain acids, like triethyl citrate or diethyl phthalate, and the diesters and triesters of certain alcohols, such as triacetin and vegetable oils, are advantageous. Though the more hydrophobic plasticizers can be difficult to mix into the water-based NCE suspension, mechanical mixing can overcome these limited solubilities to impart the desirable hydrophobic properties to the dryer sheets thus formed, so that they stand up to the stresses imposed by the heat and motion within the clothes dryer. Fatty acids can also be used as plasticizers, especially in more hydrophobic applications.

After the NCE matrix is formed, the materials that typically coat dryer sheets can then be applied using techniques familiar in the art, for example an aerosolized spray that disperses particles of wax that contain substances such as fabric softener, antistatic chemicals, and natural scents suspended therein. This waxy material then hardens on the surface of the sheet, so that it can melt off the sheet and coat the clothes in the heated dryer. In embodiments, the active agents can be pre-mixed into the NCE matrix before it is dried to form sheets. In other embodiments, the NCE matrix can be formed, extruded and dried first, with the wax containing the active agent(s) applied afterwards. Using the NCE matrix offers a greater available surface area for each sheet, as compared to conventional laundry sheets of similar dimensions, due to the increased surface area that is innate to much smaller fibers, as well as the larger number of interstices. With the greater surface area, each sheet can carry a larger volume of active agents per sheet, reducing the necessary number of sheets needed for a single load of laundry.

In embodiments, a laundry sheet can be made as a single sheet, using the NCE dispersant technology previously described, for example using a cellulosic polymer and a plasticizer to facilitate such dispersibility. As the matrix is formed from the redispersed NCEs, prior to shaping it as a single sheet, appropriate active agents, including laundry product active agents such as laundry detergents, cleaning products, and/or surfactants, bleaches, and enzymes, and optional ingredients such as chelating agents, anti-foaming agents, emulsifiers, and the like can be added. The mixture of redispersed NCEs, active agents and secondary additives can then be mixed vigorously; in embodiments, sufficient mixing can be applied so that the mixture is aerated into a foam. The mixture can then be formed into sheets and dried using conventional techniques. Once prepared and cooled, the resulting sheets can provide a stable base layer that includes within its substance core laundry agents such as detergents/surfactants or other cleaning products, but that also provides a platform for supporting other, more active agents such as enzymes and bleaching agents that would not tolerate heat treatment.

In other embodiments, NCE matrices, configured as sheets, can be used to enclose active agents in a layered arrangement. For example, two outer layers formed from NCE-based sheets can encase a laundry detergent, a cleaning product, or other active agent between them like a sandwich. Such active agents s can then be dispersed on the surface of a prepared sheet, which is then covered by another sheet, with the two layers pressed together gently to trap the active agents in a sheet "sandwich" without applying damaging heat or force to these more delicate components. The composite layered structure thus becomes available to dispense both the active agents embedded in the matrix during the sheet formation (detergents, surfactants, emulsifiers, chelating agents for hard water treatment, and the like) and any active agents or secondary additives dispersed on the surface of the matrix and not subjected to heat or excess pressure. All ingredients become available during the laundry process when the layered carrier structure is exposed to water and decomposes, releasing all of the active agents and/or other additives it supports.

The active agent can be present in a solid form, for example as a pressed powder, or suspended/emulsified in a viscous gel, or otherwise. The NCE layers, being dispersible, can release the active agent as required by the specific application, for example when contacted by water (or hot water) during a washing cycle. In other embodiments, a plurality of NCE layers can be arranged, with different active agents layered in between. Such NCE layers can have the same release/redispersion properties or different ones, which can allow for differential release of the different active agents, consistent with the selected application.

LCST polymers can be used in the laundry or soap or other cleaning sheets together or singularly, and their ratios can be chosen based upon their lower critical solution temperature, or the temperature at which their hydrophilicity transitions. The amount of plasticizer can also be adjusted to fine-tune the timing when the sheets dissolve. Moreover, tuning dispersibility by varying types and amounts of LCST polymers can be useful for applications which require different temperatures and adjusting the amount of plasticizer can allow for faster or slower dissolution.

In embodiments, an NCE-based matrix containing soap products along with fragrances, emollients, and the like, can be formulated for convenient use while traveling, so that it delivers the active agents upon contact with water, thereby allowing handwashing, dishwashing, etc., without preliminary reconstitution. As is discussed below in more detail, additives such as colors and fragrances can be incorporated in an NCE-based matrix using oil-based or water-based delivery vehicles, to affect the properties of the matrix, to accompany other active agents or to act as primary active agents themselves. As used herein, a color-producing additive can be any pigment, dye, fragrance, or other colorant that changes the perceived color of the matrix or article by absorbing or scattering different wavelengths of light along the visible spectrum. A variety of color-producing additives, for a variety of industrial, household, cosmetic, fabric, and other products, are compatible with the NCE-based formulations and matrices disclosed herein.

For example, a sheet or a formed article (e.g., a ball or cube) can be formed using an NCE-based matrix with a fragrance in the matrix interstices that can be used for odor control purposes, for example in a closed space. In more detail, an NCE-based matrix can be used to include odor-blocking chemicals or natural scents adapted for release in close quarters that have high levels of odoriferant materials, for example in closets, gym bags, suitcases, etc., or adapted for use in personal articles likely to be odorific (e.g., shoe inserts or liners). The NCE matrix adapted for these purposes can incorporate plasticizers or other additives to tune the release of the anti-odor agents or to adapt their release to certain environmental conditions (for example, shoe liners that emit odor-control substances when in contact with body-temperature feet). Analogously, an NCE-based matrix can be formulated with a deodorant or antiperspirant substances in the matrix interstices, with the NCE-based matrix serving to permit a more durable application of such products to the skin.

The base formulation for odor-control articles can include a NCE source treated with a plasticizer such as glycerol and a cellulose polymer such as methyl cellulose, with a ratio of these two actives to dry NCEs in the range of 1:1 to 12:1. This creates the NCE base matrix, in which other, more hydrophobic chemicals such as aromatics and oil-based scents can be suspended, producing a more hydrophobic environment that can offer additional advantages such as preventing breakdown from moisture or from contact with aqueous solutions.

Whether intending to control odor, mask odor, or produce odor, these odor-related active agents (e.g., anti-odor, odor-masking, or odor (fragrance)-producing agents) can be mixed into the NCE base matrix at a desired concentration (e.g., in a range between about 1% and about 30% or between 10% and about 20%) to achieve the necessary scent strength. When finished, a viscous liquid is formed that is spreadable to form sheets having a thickness that can typically range from 0.1 mm to 3 mm, or the viscous liquid can be formed into any other desired shape by using techniques familiar in the art for forming articles. For films or sheets as described above, after spreading they can be dried in a low temperature oven to form a dry, paper-like layer that can be used separately or incorporated into other articles of manufacture. Articles thus formed, whether flat sheets or three-dimensional shapes, can constantly release the desired odors at a rate determined by the amount of plasticizer used. The flexible geometry that a sheet provides can be useful in harder-to-access areas, such as sneakers or thin crevices in a household. It is understood that different geometries will distribute scents differently. In embodiments, scents can be suspended inside these sheets or shapes, for example, in a pod or a casing.

In embodiments, a variety of scents can be employed with the systems disclosed herein. The term "scent" as used herein refers to the variety of odors that can be deliberately incorporated in and delivered by the matrices, shapes, and vehicles as described. For example, pleasant scents can be employed for cosmetic or aesthetic purposes, or to camouflage unpleasant odors. Scents can be employed for medical, veterinary, or agricultural purposes, to act as insect repellants, pesticides, pheromones, growth hormones, or the like. Scents can be sourced from volatile aromatic compounds, such as essential oils, hydrosols, perfume microcapsules, etc. Exemplary sources can incorporate biological oils and chemical sources suspended in solution for easy application or mixing. Other sources for scents can be aqueous-based, such as hydrosols. The biodegradable nature of the NCE-based vehicles makes them especially useful for delivering scents or other active agents that are to be released naturally into the environment: the decomposition of the vehicle (e.g., a sheet) facilitates the release of the active agent: the rate of release can be controlled through careful selection of the active agents and vehicle components, with a modification of the ratios of each component.

Other examples of scent-based technologies based on the formulations disclosed herein include without limitation insecticides for the agricultural sector, perfumes and odor neutralizers for household use, and pet hormones to encourage calm behavior around the home. By controlling the rate of release through careful manipulation of the base technology, the applications can be personalized for various consumer needs, for example, for agricultural products that release pesticides quickly during planting season and more slowly when the plants are fully grown.

In embodiments, a NCE matrix containing agricultural active ingredients can be applied to agricultural products to be used in treating them, where such treatments can include those additives, fertilizers, pesticides, hormones, nutrients, or other treatment agents intended to improve the life or health or post-harvest condition of the agricultural product, or to ameliorate an adverse condition pertaining to the product, as would be understood by artisans of ordinary skill in the art. As an example, a NCE matrix containing agricultural active ingredients can be used as a spray-on coating for plants or seeds. For living plants or plant materials, a NCE matrix can contain active agents intended to repel or kill insects, fungi, and the like, or can contain nutrients or other beneficial agents, or other agricultural active ingredients. For seeds, NCE coating can be used to mark or designate seeds, allowing color grading or other differentiation, or can repel moisture, dust, or other physical contaminants. NCE matrices can support active agents intended to enhance growth or protect against pests and fungi, including sustained release formulations of such active agents, and can furthermore protect against mechanical damage. In embodiments, the NCE matrix for seed coating can contain precisely formulated agents (such as fertilizers, micronutrients, crop protection chemicals and biologicals, temperature-sensitive polymers, water-retention materials, colorants, and beneficial organisms, etc.), which can be dispensed over appropriate time intervals following application. NCE matrices can further be formed into structures that can support preloaded seeds at precisely positioned spacings, with nutrients, fertilizers, or protective substances like weed-killers embedded within the matrices and optionally combined with materials that can retain water around the seed itself, thereby facilitating seed planting and optimizing seed growth.

For example, as described previously, matrices comprising odoriferant materials can be readily formed from NCE matrices, optionally in combination with plasticizers to control the release of the odoriferant. This technology can be adapted for agricultural purposes, for example with the use of pheromones as the agricultural active ingredients. Pheromones are understood to be secreted or excreted chemicals that trigger a social response in members of the same species. While they may not possess "odors" as the term is commonly understood, pheromone receptors are typically located in the olfactory epithelium or vomeronasal organ, indicating that they are processed by similar pathways as conventional. Pheromones are thus considered odor-related active agents for the purposes of the present disclosure.

It is known that certain pheromones have use in the agricultural industry as pesticides or artificial growth hormones. Pheromones can be suspended in NCE matrices and formed into sheets or formed articles, whereby the pheromones are released into the environment at a controlled rate as the NCE matrix decomposes. The rate of release can be controlled through the careful selection of plasticizer and modification of the amount of it in the matrix substrate. Hydrophobicity can be controlled through the selection of an additive imparting hydrophobic properties to the matrix, such as a cellulosic polymer additive (e.g., a more or less hydrophobic polymer). NCE matrices containing more hydrophobic materials will take longer to break down, releasing the pheromones into the environment at a slower rate, encouraging long-term growth. An additional advantage of this technology is the contribution of cellulose to the soil, which encourages the activity of helpful insects in the environment to aerate the soil and break the cellulose down into useful materials such as carbon dioxide for the plants.

It is understood that other active agents having agricultural effects can be similarly incorporated into NCE matrices for applications to growing plants. For example, in embodiments, growth hormones can be included in the matrices and released in a controlled manner, as described above. In other embodiments, insecticides, fungicides, pesticides, and the like can be incorporated into NCE matrices. For these purposes, the matrix itself can include plasticizers to facilitate the diffusion of the active agents into the ambient air if this is the appropriate mechanism of action; such plasticizers can advantageously be hygroscopic to help the diffusion of the active agents if they are to be airborne. In order to hold the active agents within the NCE matrix without premature release and without damaging the matrix itself, the matrix material can be thickened using a thickening agent such as cellulose polymers, starch, gelatin, or the like. Similar technology can be used for insect repellants, such as DEET, permethrin, picaridin, and the like. These materials can be incorporated into NCE sheets and applied directly to the skin or to articles of clothing. As the sheet dissolves, the residual active agent is deposited locally, continuing to provide insect repellent activity. Appropriate selection of plasticizers can prolong the release of the insect repellants, to prolong protection.

In addition, matrices used for agricultural purposes can be coated with or formulated with hydrophobic components to protect the agricultural active agents and prevent them from being washed off after application. This ability to protect the active agent and provide for controlled release can be useful for dispensing fertilizers to plants over a prolonged or predetermined period of time. By contrast, current fertilizer formulations are water-soluble, so that they can be easily washed away on rainy days. It is understood that a more hydrophobic selection of components for the NCE vehicle (promoted with the selection of more hydrophobic cellulose materials, such as methyl cellulose, or with the addition of oils or waxes) will take longer to break down in a moist environment, such as in the ground or in an area with high humidity, releasing the pesticides, hormones, fertilizers, etc., into the environment at a slower rate, encouraging long-term growth. An additional advantage of this technology is the contribution of cellulose to the soil, which encourages the activity of helpful insects in the environment to aerate the soil and break the cellulose down into useful materials such as carbon dioxide for the plants. The NCE-based technology disclosed herein can cooperate with the agricultural active agents to encourage healthy growth of plants for stronger, more abundant crops.

ii. NCE Matrices as Structures: Dissolvable Properties

NCE matrices have mechanical properties due to their incorporation of the NCEs themselves in a structural framework. The matrices can thus be used as supporting or enveloping structures for formed articles that have advantageous mechanical properties such as strength and stability but that are also engineered to be dissolvable at an appropriate time for consumer use.

This property allows containers to be constructed that have sufficient durability to retain their contents during consumer use, but furthermore to allow for their ready decomposition and biodegradability after use. This property allows containers to be constructed for more ephemeral purposes, such as a container for a fertilizer or agricultural product that is intended to dissolve over a short period of time in order to release the product into the environment. This property also allows containers to be constructed for immediate dissolving upon encountering water, for example for delivering active agents for laundry or other home care purposes.

As an example, sheets, strips, and the like formed from a NCE matrix can be used to provide wrappers or containers for enveloping or otherwise delivering active agents within, thus providing an easily dissolving (dispersible) vessel for useful materials, allowing such materials to be dispensed conveniently by the consumer. For example, active agents such as a cleaning product, a laundry detergent or a dishwasher soap can be enclosed in a biodegradable sheet comprising a dispersible NCE matrix. One or more compartments can be formed with the NCE-based wrapping material so that the various active agents can be kept separate, if needed, within a single article. In embodiments, sheets formed from NCE matrices can be joined together to form containers for enveloping active agents such as laundry products as a payload within the closed NCE envelope; such sheets can themselves also contain active agents in their interstices, so that more than one type of laundry product is delivered, with each one kept separate from the other(s). A differential solubility profile can permit the active agent in the NCE-matrix sheet itself to be delivered first, followed by sufficient dissolution of the encapsulating sheet structure surrounding the payload to impair its integrity and permit delivery of the payload.

In embodiments, an NCE-based wrapping material can enclose a paste or gel comprising a laundry detergent or other cleaning product, for example in powdered or in gel or liquid form, optionally including other active agents such as bleaches, enzymes for stain removal, fabric softeners, and the like. In embodiments, active agents such as are exemplified above (e.g., cleaning or laundry products) can be enveloped in an NCE-based wrapper to form a pod-like container for the active agents. In an embodiment, a wrapper formed from a NCE matrix sheet can wrap completely around the product, or a wrapper can be positioned above and below the active agent and sealed to enclose the active agent. Sealing the two NCE wrapper sheets can be performed using heat (searing), or by applying a natural polymeric adhesive to stick them together. In embodiments, a thin and lightweight sheet formed from a redispersible matrix and weighing about 1 gm can be shaped as a pod or an envelope to contain up to about 30 gm of a detergent powder in its interior. In other embodiments, the NCE based matrix can be extruded from a circular die as an open, elongate tube. The tube with or without active agents inside can be cut to desired lengths whose ends can be sealed by pinching, searing, or gluing. Alternatively, the hollow tube can be cut to the desired lengths, with one end sealed, following which the desired ingredients are loaded in the hollow interior.

In yet other embodiments, the NCE-based matrix can be used as a wrapper or a container for a cleaning product such as a toilet bowl cleaner, allowing the fabrication of a disposable, biodegradable toilet cleaning pad or cleaning brush that be used instead of the conventional system for toilet bowl cleaning comprising a reusable brush and a cleaning product to be dispensed in the toilet bowl. In such an embodiment, the cleaning product can be enveloped within one or more external NCE matrices to form a single-use, flushable, biodegradable cleaning pad or brush, which can be attached to a wand, extendible member, or other applicator by the user before employing the cleaning pad to scrub the surfaces of the toilet. At the conclusion of the cleaning process, the cleaning pad can be detached from the applicator to be flushed away with the water in the bowl that has been used for rinsing off the cleaning product. Advantageously, the cleaning pad can be detachable by the user through a mechanism on the proximal end of the applicator, so that the user need not directly contact the flushable pad or brush to remove it. As an additional advantage, the NCE-based matrix containing the cleaning product can have abrasive properties (as described below in more detail), and those properties can be optimized so that the scrubbing surface of the pad is adapted for cleaning the surfaces of the toilet bowl. This system, comprising an applicator and a flushable pad or brush, is a hygienic alternative to conventional toilet bowl cleaning systems because there is no multiuse toilet brush that must be stored in between exposures to the contaminated surfaces in the toilet. Instead, the applicator can be made of a smooth plastic material that resists the attachment of contaminated material; contaminants instead remain attached to the NCE-based matrix exterior of the cleaning pad, and the pad itself is flushed away. The biodegradability of the NCE-based matrix allows the pad to decompose quickly after cleaning has been accomplished, to minimize the risk of obstructing plumbing after flushing.

A paste or gel to be enclosed within the dispersible NCE-matrix-based container can be formed by suspending the active agents in a vehicle formed from a water-soluble, non-aqueous, viscous liquid polymer such as poly(propylene) glycol, polyethylene glycol, polyethylene oxide, polyoxyethylene, and the like, and their derivatives. A thickening agent can be optionally added that is soluble in the water soluble, non-aqueous, viscous liquid polymer, for example cellulose polymers such as hydroxypropyl methyl cellulose, methyl cellulose, etc., optionally in combination with a dispersible (i.e., water soluble), hygroscopic plasticizer such as glycerol. In embodiments, the paste or gel can be formed by combining detergent and a cellulose polymer or combination of polymers in ratios between 8:1 and 15:1, with a range of a 2:1 ratio to 8:1 ratio of a dispersible viscous polymer to the active modifiers of the cellulose polymer and hygroscopic plasticizer, and a ratio between 50/50 and 95/5 of cellulose polymer to hygroscopic plasticizer. A composition comprising these substances can create a highly viscous, gel-like medium within which cleaning or laundry products such as detergents, bleach, enzymes, fabric softeners, and the like can be suspended. In embodiments, a powdered or other concentrated form (e.g., concentrated liquids, gels, emulsions, and the like) for the active agent(s) offers advantages, for example, allowing the co-presence within the gel of several different chemicals that ordinarily cannot be physically combined, due to their interaction if they are mixed together as aqueous fluids; in powdered or other concentrated form, these chemicals can coexist within the gel, without requiring separate compartments to keep them apart. Moreover, due to the powdered or other concentrated form of the active agent(s), the volume for each unit can be decreased to improve shipping efficiency. This composition, containing the active agent(s) suspended or emulsified within the paste or gel matrix can then be packaged within sheets or wrappers formed from NCEs as described herein to create sealed single-use containers such as single-chamber or multi-chamber pouches, pods, or otherwise suitably shaped packets that can be put directly into the washing machine or dishwasher, using safe, biodegradable materials that dissolve readily upon contact with water to release the contents. It is understood that the active agents dispersed in the polymer gel medium can be arranged in order to facilitate specialized cleaning, for example, in layers, such as a layer of bleach-containing gel being attached to detergent gel for extra strength cleaning, and they can be separated by layers of sheet material in between.

The NCE-based wrapper encasing the active agent(s) can be further engineered to tune the release of the active agents, for example creating a time-release container or a container that requires a certain water temperature before dissolving. In embodiments, this timed, or tuned, release can be done by adjusting the amounts of cellulose additives (dispersant material) that is able to dissolve at different times. For example, one or more LCST polymers can be used to form the NCE-based wrapper, and their ratios can be chosen based upon their lower critical solution temperature, or the temperature at which their hydrophilicity transitions. The amount of plasticizer can also be adjusted to fine-tune the timing for dissolution of the wrapper. Moreover, tuning dispersibility by varying types and amounts of LCST polymers can be useful for applications which require different temperatures and adjusting the amount of plasticizer can allow for faster or slower dissolution, for example if wrappers with different properties are used for segregating different compartments containing different active agents.

iii. NCE Matrices as Structures: Barrier Properties

NCE matrices prepared for use as containers or as films can be optimized for these applications to impart oil and grease resistant (OGR) properties and/or water-vapor or water resistant (either, WVR) properties to the NCE-based structures. WVR properties are often measured by the water vapor transmission rate (WVTR), which measures a material's water vapor permeability in units of $gm/m^2/day$, or in $g/100\ in^2/day$. Collectively, those coatings, formed articles and material treatments that improve resistance to oil and grease permeability and/or that improve resistance to water vapor permeability, and/or that improve resistance to other fluids (liquids or gases) are termed "barrier treatments," or "barrier-producing" materials. The resistance to selected fluids that they impart to the formed substance or substrate matrix, such as OGR and/or WVR properties, are termed "barrier properties." Barrier properties can be tuned to permit differential permeability of various fluids, or selected degrees of permeability of various fluids. As an example, in embodiments a barrier-producing formulation may impart both OGR and WVR properties to the article it treats, with the relative strength of each property being tunable by adjusting the ingredients selected for the formulation itself, and/or by adjusting the relative amounts of its ingredients, for example to emphasize hydrophobicity or oleophobicity.

In embodiments, barrier formulations can be prepared to emphasize OGR properties or WVR properties or both; in embodiments, barrier formulations can include both types of properties, and the formulation components can be tuned to accentuate either the OGR or the WVR properties or to balance them. The barrier formulation can comprise such ingredients as NCEs, cellulose polymers, filler particles, plasticizers, film-forming biopolymers, and the like, with different constituents and different amounts of such constituents being selected to emphasize the OGR or WVR features in the barrier treatment, as applicable to the particular article being treated and formed. For example, a range of cellulose polymers exists, with the various polymers having different degrees of hydrophobicity or oleophobicity, so that a cellulose polymer can be selected to produce the desired degree of OGR and/or WVR. OGR technologies may include cellulose derivatives, and specifically ones that are more hydrophobic. Overall, the cellulose derivatives previously described are oleophobic (hydrophilic), so it would be beneficial to mix in other materials that are more hydrophobic into the matrix to provide more water resistance, or overall more OGR/VWR. For example, methyl cellulose provides good oil/grease resistance, but not as much water-resistance. A mixture of methyl cellulose and cellulose acetate can be provided to tune for both OGR and WVR properties. LCST polymers discussed work well for oil resistance, but the films/coatings created with them are soluble at room temperature, causing water resistance properties to be less efficient. Cellulose acetate and lipids are some examples of additives that can be used to tune OGR coatings to be more hydrophobic, and the combination of this with a more oleophobic material can provide both oil and water resistance. Similarly, certain fillers have more hydrophobic or olcophobic properties: for example, a filler such as wax can be selected to increase hydrophobicity, or, for example, a large surplus of NCEs can be added as pore-blockers to increase oleophobicity. Fatty acids may also be used to increase hydrophobicity. Advantageously, the barrier formulation can be sprayable to permit easy application, whether to the surface of a formed article or to the substrate itself for mixing in.

In more detail, depending on the balance and amounts of ingredients, barrier treatment agents can be formulated for use in three general categories: 1) having a barrier profile with balanced OGR and WVR properties, and both OGR and WVR to an effective degree; 2) having some WVR but substantial OGR; and 3) having some OGR but substantial WVR. Articles treated with Category 1 barrier formulations can be used for applications such as food packaging in which both oil repellency and water repellency are advantageous. Articles treated with Category 2 barrier formulations can be used for those applications in which oil resistance is the more important attribute, for example in containers for oils or greasy materials, and for packaging for premeasured amounts of oil-based products such as salad dressings or cosmetic lotions, or for use as more durable vessels that can contain motor oil and similar fluids, instead of the metal containers in use for this purpose. Articles treated with Category 3 barrier formulations can be used for those applications in which water repellency (even waterproofing) is the more important attribute, for example in coffee cups and six-pack holders for beverage cans, or in grocery bags and other containers or wrappers intended to be substantially water-resistant or leak-proof.

In embodiments, film-forming biopolymers can be added in barrier formulations, for example in those formulations intended for mix-in use. As used herein, the term "biopolymer" refers to those polymers that are produced by a living organism during its lifespan. Such biopolymers can include, without limitation, exopolysaccharides such as bacterial cellulose, kefiran, pullulan, levan, gellan, and other polysaccharides such as alginate, celluloses, carrageenan, gum Arabic, starch and plant glycomannans-like locust bean gum, mannan, guar gum, and the like. Biopolymers can also include biopolyesters such as polyhydroxy-alkanoates and polylactic acid derivatives. Advantageously, certain exopolysaccharides such as pullulan, kefiran, cellulose, levan, gellan, and the like can be used to form films, such as are used in packaging applications. The addition of biopolymers useful as film formers or having other useful mechanical or barrier properties can allow the barrier formulation to be tuned and customized for particular purposes.

In embodiments, additional measures may be useful to address the porosity of the NCE matrix within which the formulation is to be supported. Additions to the base formulation can be provided, for example stearic acid or other long-chain fatty acids to enhance the barrier's hydrophobic properties, or wax beads as pore fillers to produce a more hydrophobic base substrate for formed articles.

Under certain circumstances, pore closure within the matrix is advantageous to permit the barrier treatment to work effectively or to improve its efficacy. If pore closure is desired, barrier treatment formulations (for example, comprising cellulosic polymers with varying hydrophobicity, plasticizers, and NCEs) can be used in combination with additional pore closure materials, such as filler particles to block the pores within the NCE matrix to improve the ability of the matrix to block oil, grease, and/or water. Such filler particles can include, without limitation, large or small particles of any shape, or mixtures of different sizes and shapes, made from natural or artificial materials, including organic or inorganic components; by way of illustration, particles useful for this purpose can comprise, without limitation, sand materials, ceramic materials, resinous materials, glass materials, polymeric materials, rubber materials, organic materials such as nutshells that have been chipped, ground, pulverized or crushed to a suitable size (e.g., walnut, pecan, coconut, almond, ivory nut, Brazil nut, and the like), seed shells or fruit pits that have been chipped, ground, pulverized or crushed to a suitable size (e.g., plum, olive, peach, cherry, apricot, etc.), chipped, ground, pulverized or crushed materials from other plants such as corn cobs, specific particles such as solid glass, glass microspheres, fly ash, silica, alumina, fumed carbon, carbon black, graphite, mica, boron, zirconia, talc, kaolin, titanium dioxide, calcium carbonate (e.g., precipitated calcium carbonate (PCC)), calcium silicate, and the like, as well as combinations or composites of these or similar different materials. Advantageously, in certain embodiments filler particles can be selected that can be hydrophobic in nature, or that can be made hydrophobic (e.g., functionalized PCC), for example by linking or coating them with a hydrophobic material such as stearic or oleic acid. In embodiments, the filler particles can comprise waxes, either as the substance for the particle itself or as a coating for other particles, and these waxes can be in wax form or emulsion form (oil in water wax emulsion). For example, a waxy substance such as beeswax, soybean wax, carnauba wax, and the like, can be used, either as a base particle or as a coating for other filler particles. As used herein, the term "wax" refers to any hydrocarbon that is lipophilic and a malleable solid near ambient temperatures, typically having a melting point above about 40° C. As examples, waxes can include long-chain aliphatic hydrocarbons typically having 20-40 carbon atoms per molecule, or fatty acid/alcohol esters typically containing from 12-32 carbon atoms per molecule, such as myricyl cerotate, found in beeswax and carnauba wax. Filler particles can be mixed into the barrier formulation to impart pore-clogging functionalities.

With or without the presence of pore-clogging filler particles, it is desirable in certain embodiments to prepare the barrier formulation as a viscous suspension; it has been determined, for example, that viscosity enhances the pore-clogging feature of the formulation and improves its oil-and-grease-resistant properties. However, in other embodiments, it is advantageous to prepare a more dilute suspension, for example when used as a mix-in formulation: in embodiments, using a less viscous barrier formulation can improve the mixing of the barrier-producing ingredients with the pulp or pulp-based matrix substance being used for shaping the formed article. As used herein, the term "pulp-based" refers to those materials that have been derived from pulp by processing, forming, or treating while retaining pulp or pulp derivatives within their substance. Pulp and pulp-based materials can be used with the formulations, compositions, and methods disclosed herein, to be formed or shaped as components of or substrates for articles of manufacture in any useful shape, such as sheets, fibers, solid articles, molded articles, etc.

In embodiments, NCE-based OGR and WVR materials as disclosed herein can be used as barrier treatments, such as (i) coatings on top of the matrix or on top of articles made therefrom to impart barrier properties thereto, (ii) mix-in additives incorporated in other compositions or substances that are themselves used to form articles, to impart barrier properties thereto, (iii) films or packages that possess barrier properties, for containing other substances or materials, or (iv) any combination of the foregoing. In more detail, OGR and/or WVR formulations can be used as coatings, or can be mixed into an NCE-based slurry and be shaped (e.g., thermoformed) into a product. For example, in embodiments, containers formed from NCE matrixes can be prepared having OGR properties and/or WVR properties, enabling the containers to securely confine and deliver liquids or gels to the consumer for other purposes.

In embodiments, the barrier-producing ingredients can be mixed into the NCE-based matrix formulation (as described above) at any concentration; then, before molding/thermoforming takes place, the mixture can be heated to just above the lower critical solution temperature of the LCST polymer component of the barrier formulation. This procedure allows the LCST polymer dispersed within the mixture to precipitate (or "crash out") onto the surface of the fibrous, NCE-bearing matrix. In other embodiments, the barrier-producing formulation can be applied more superficially to an article of manufacture, using conventional application procedures such as painting or blade painting, curtain coating, and the like, or spraying if the formulation is of a viscosity that is compatible with the selected spraying apparatus.

A film, sheet or formed article having barrier properties provides important advantages when employed in commercial products. For example, an OGR or WVR pouch, pod, or other packaging article formed from NCEs as described herein can serve as a container for condiments, dressings, or other liquid or gelatinous food substances, allowing the consumer to open the package and dispense the food substance as desired. Such packaging can conveniently contain and dispense aqueous or oil-based food substances like soy sauce, ketchup, mustard, mayonnaise, salad dressings, dairy products, and the like, thereby reducing the plastic waste associated with conventional packaging for such food substances.

The NCE wrapper material can be tuned to maximize other protective elements of the package, to optimize oil resistance for oils or oil suspensions or to optimize water resistance for aqueous solutions or suspensions, to add strength, or to reduce gas permeability to provide for more hermetic packaging properties. For example, wrappers and sheets formed from NCEs having OGR and/or WVR properties can be used as components of or entire containers for liquids such as milk (e.g., shelf-stable milk cartons), to be sterilizable by techniques such as ultraviolet sterilization and other methods familiar to artisans of ordinary skill. In embodiments, these OGR and/or WVR packaging materials can be transparent or translucent, with superior mechanical properties such as tear resistance or rigidity, offering a viable alternative to conventional packaging and hermetic films made from polyolefins. In embodiments, the OGR and/or WVR materials incorporating NCEs, as disclosed herein, can be modified by adding additional polymers or particles to the matrix material (e.g., PVA, PVOH, hydroxyethyl butyrate, exfoliated clay, and the like), to improve their hermetic properties.

iv. NCE Matrices as Structures: Intrinsic Properties

NCE matrices possess certain intrinsic mechanical properties, including hardness, toughness, brittleness, stiffness, cohesion, durability, impact resistance, optical transparency, and the like, that can also be improved or tuned for specific applications by incorporating NCEs prepared as disclosed here, optionally in conjunction with appropriate secondary additives. Such intrinsic mechanical properties can be exploited in useful articles. These intrinsic mechanical properties can be advantageous alone, or in combination with other characteristics of NCE matrices such as their ability to act as carriers, to act as dissolvable containers, or to act as oil, grease, and/or water-resistant barriers. In embodiments, an NCE matrix can be prepared having advantageous intrinsic mechanical properties for a particular application, while also providing a suspending framework for embedded active agents.

For example, by engineering the intrinsic mechanical properties of the NCE matrix to achieve a desired degree of hardness, strength, and toughness, nano-scaled abrasive compositions can be formed. It is understood that, during abrasion, the surface of the abrasive material forms an irregular interface with the abraded surface that causes particles on the abraded surface to be torn off or worn down. Since the NCE matrix is formed with its surface irregularities on a nano-scale order of magnitude, these matrices can be engineered for applications requiring minimal, gentle abrasion. As examples, an NCE matrix can be used for minimal abrasion as a removal pad for face makeup, or a pad for skin exfoliation. In other embodiments, an NCE matrix can be combined with soap products or body/facial cleansers as an exfoliant. In yet other embodiments, the NCE matrix can be used for minimal abrasion to remove dental plaque in dentifrices for oral hygiene, or as dental products for professional use. An NCE matrix formulation can be particularly advantageous for dental products such as toothpaste or tooth powder by allowing the abraded dental plaque to adhere to the extensive surface area of the matrix itself to facilitate the removal of the plaque particles. In yet other embodiments, an NCE matrix can be used to abrade uneven or damaged biological surfaces as may be found on bones or in blood vessels. In embodiments, the NCE matrix used for abrasion purposes can support embedded active agents, such as an anticoagulant agent to be applied to an abraded arterial plaque to prevent subsequent adherence of platelets during the healing period.

Appropriately engineered NCE matrices are suitable for use as household scrubbers, cleaners, and wipes. For example, an NCE matrix material can be shaped as a scrub or a sponge, optionally preloaded with cleaning chemicals. In such articles of manufacture, the NCE architecture can provide an extensive surface area within the matrix, permitting extremely high capture of oil, grease, dirt, or other spilled materials while also providing abrasiveness that facilitates scrubbing. As a further advantage, the NCE matrix is itself made of plant-derived products, and is disposable and compostable.

Appropriately engineered NCE matrices can be readily transformed into sheets or liquid foams that can be dried to form substitutes for conventional articles such as paper packaging or Styrofoam. Non-foamed sheets can be used as substitutes for paper wrappers, butcher paper, sandwich wraps, and the like, where the properties of a foam are not needed; foams can be used in specialized situations where properties such as thermal insulation are advantageous, or where the light weight per unit of volume is advantageous, as in packing peanuts. In embodiments, barrier properties can be introduced into the foam using the techniques for rendering the formulation more hydrophobic or oleophobic, as described above. In embodiments, oil and grease resistant properties can be imparted to the foam by rendering some or all of the NCE particles more oleophobic, and/or by using the matrix to support oleophobic coating materials, and/or by introducing other oleophobic additives; similarly, water-vapor resistant properties can be imparted to the foam by rendering some or all of the NCE particles more hydrophobic, and/or by using a matrix to support hydrophobic coating materials, and/or by introducing other hydrophobic additives. As described herein, foamed or non-foamed formulations can be customized to emphasize either the oleophobic or hydrophobic properties, and such formulations can exhibit both types of properties to greater or lesser degrees.

In more detail, materials comprising NCE matrices can offer replacements to conventional foam products such as are found in synthetic Styrofoam packing materials. Conventional packing materials and containers are lightweight, cushioning, and water-repelling, thus well-adapted for their end-uses; however, these materials are made from petroleum-based plastics like polystyrene, which cannot be recycled and which therefore are relegated to landfills, where they take centuries to decompose. Foamed NCE matrices can offer biodegradable alternatives with good intrinsic mechanical properties, or NCEs can be used with other biodegradable materials to improve their properties for uses such as packing materials, as will be described in more detail below. In order to form sheets or liquid foams, the NCEs to form the matrix can be treated to permit redispersibility, as described above. In embodiments, a slurry of 2-3% redispersed NCEs can then be mixed with a cellulosic polymer and an optional plasticizer, and/or combined with a hydrophobic or oleophobic material in order to impart the desired barrier properties; in other embodiments, the hydrophobic or oleophobic material can replace the cellulosic polymer, while in yet other embodiments, the cellulosic polymer itself can provide the desired hydrophobicity or oleophobicity. A barrier-producing additive, for example a hydrophobic starch, a hydrophobic cellulosic polymer, a fatty acid, surfactant, or a water in oil or wax emulsion, can be added in ratios ranging from 1:1 barrier additive to NCE to 15:1 barrier additive to NCE, and preferably from 3:1 to 9:1. In embodiments, foaming can be produced easily with NCE suspensions, because of the high viscosity of these materials and their response to vigorous agitation or whipping, and barrier properties can be readily introduced into the foam. Adding surfactants to an NCE suspension can facilitate foaming. Once the NCE suspension has been foamed, flash-drying can lead to a locked-in foamy texture in sheets or formed articles. As examples, rolling up or vacuum molding unfoamed or foamed sheets of NCE matrices can create thermally insulting, lightweight cups, plates, bowls, food wrappers, takeout containers, or trash bags having the added advantage of biodegradability as an NCE-based product. As an example, high efficiency, lightweight, thermal insulation can be produced from a dried NCE foam, with barrier properties (OGR and/or WVR properties) available as optional, customizable features.

The durability of the NCE matrix when dried on the skin can support a variety of other cosmetic and medical products, including without limitation, bandages and wound dressings based on NCE matrices bearing disinfection or coagulation aids, vehicles for sustained delivery of health or wellness agents such as insect repellants, anti-itch medications, analgesics, topical anesthetics, CBD oil and the like, or diagnostic products or monitors, e.g., for glucose monitoring, ionic conductivity, pH, and the like. In other embodiments, the NCE matrix can be ingestible, for use e.g., with probiotics or pharmaceuticals, providing controlled and slow release.

The use of NCE matrices is particularly advantageous with active agents in certain personal care applications because of the optical transparency of the NCE suspension, for example hair hold formulation and cosmetics. In embodiments, shampoos, hair conditioners, hair hold, and hair color preparations can be formulated by including the active agents within the NCE matrix, with the matrix then drying as a transparent layer on the underlying hair shaft surface. Hair products for temporary hair styling can also use NCE matrices for retaining hair in a particular shape or style. In more detail, it is understood that hairspray, mousse, gels, and the like have been designed and are used to hold many different hairstyles in place for hours at a time. These conventional products tend to use harsh chemicals to provide desired "hold," and products lacking this category of chemicals tend not to produce satisfactory hair hold: they may not hold as well, or they may provide a "crispy" feeling to the hair, or they may produce a stiff or unnatural look. As an alternative, NCE matrix formulation can include active agents such as chitosan that allow the NCE matrix to adhere firmly to hair strands and to impart shape-hold benefits. The product can be washed out of the hair with water and ordinary shampoo. An NCE-based formulation with the addition of chitosan or similar reinforcing secondary additive can produce durable hair hold with a soft, natural feel, without employing harsh chemicals.

While the NCE matrix can be used with a single active agent, it can also support combinations of hair care products within a single formulation, for example a shampoo, conditioner, and shape-hold agent all applied at once as a single product. NCEs can also be used to impart color onto hair in an easy, gentle manner without the use of harsh chemicals. In other embodiments, NCEs can be precolored before being suspended, and/or can incorporate color-bearing particles such as lignins within their matrices, allowing convenient application to hair, for example to darken grey hair, without requiring the harsh chemical treatments used in conventional products.

In other embodiments, NCE matrix formulations can be used for applying cosmetic or skin care (i.e., treating skin disorders or skin conditions such as wrinkles or hyperpigmentation) products. As an example, a skin cream can be formulated by suspending skin-treating substances (such as vitamins, lipoic acid, collagen, emollients, sunscreens, and the like) in the NCE matrix, to form a product that is invisible on the skin after application due to the optical transparency of the NCE matrix. As another example, NCE-based creams or lotions can be spread on the skin surface to smooth it and flatten out wrinkles. With higher concentrations of NCEs, the formulation contracts as it dries and pulls the skin taught; with appropriate positioning and directional orientation of the applied formulation, it can exert a force that counteracts skin wrinkling or that offers a smoothing of the skin surface. As yet another example, an NCE matrix for a sunscreen or sunblock is particularly advantageous, because of its intrinsic strength following application, so that it forms a durable layer of sunscreen protection on the skin. In embodiments, pigments can also be added to mask the chalky appearance of sunblock agents such as zinc oxide or titanium dioxide. As another example, a skin cream or face mask can be formulated as a shape-hold material that temporarily flattens wrinkles after application and drying, due to the strength properties of the NCE matrix once dried; in embodiments, the matrix can be engineered to contract upon drying, thus exerting force on loose or wrinkled skin in advantageous directions.

Vehicles can be prepared for medical skin treatments or transdermal pharmaceutical delivery using NCE matrices. Pharmaceutical products, nutraceutical products, moisturizers, antioxidants, and the like can be incorporated into NCE matrices and applied to the skin so that the active agents can pass through the matrix into the skin. As an example, an application of a NCE matrix containing moisturizers, antioxidants and topical retinol could be used as an overnight mask, which would keep the active agents in place while offering a dry external surface for contacting bedclothes.

Similarly, a NCE matrix can be used for applying a pharmaceutical or other beneficial product to a localized area of the skin. Topical products for acne or rosacea (such as salicylic acid, azelaic acid, topical retinoids, benzoyl peroxide (for acne), metronidazole, ivermectin, (for rosacea), topical antibiotics (for both) embedded in a NCE matrix can be applied to affected areas for local treatment. While the NCE matrix is typically translucent or transparent, pigments can be included to render the product opaque and conceal the lesions undergoing treatment.

NCE matrices can be engineered for transdermal delivery of pharmaceutical products, especially those used as sustained release agents. As examples, active agents such as nicotine, opioids, hormones, nitroglycerin, methylphenidate, MAO inhibitor antidepressants, clonidine, scopolamine, Vitamin B12 and cyanocobalamin, and the like, are compatible with delivery as transdermal patches that can be formed from NCE matrices. For certain applications, the patch formed from NCE matrices can support an array of microneedles, thus forming a microneedle transdermal patch that can be used for controlled release of other pharmaceutical products. The presence of the NCEs in these patch products can improve the strength and durability of the patches.

A variety of biomedical and cosmetic articles of manufacture can incorporate NCEs as a matrix for the delivery of medical or cosmetic active agents and can further incorporate NCEs as a filler for strength enhancement. When used as a matrix, NCEs can form the framework for roll-on, spread-on, or spray on patches or liquid bandages. Such devices can be used to deliver pharmaceutical, nutraceutical or cosmetic products as active agents, including collagen, vitamins, retinoids, hyaluronic acid, and the like. Such products can be delivered as a liquid form factor, for example as a concentrate that can be further diluted or as a ready-to-use liquid, or as a solid form factor to be dissolved or suspended in water by the consumer, who then applies the reconstituted formulation to the affected area. In embodiments, the NCEs can be applied to form a film, i.e., a continuous layer over the affected area, to cover and protect skin injuries to encourage healing. A liquid NCE-based formulation can dry to form a thin, solid, flexible protective barrier, optionally transparent or translucent so that healing can be monitored. Antiseptics or antibiotics or other specialized active agents can be included in the formulation to prevent or combat infection in the area covered by the barrier.

NCE formulations having oil, grease, and/or water-resistant properties can be combined with NCE matrices, so that the film applied to the skin is more likely to stay in place and resist wear and tear. For applications incorporating NCEs as delivery vehicles for active agents (such as creams, patches, bandages, and the like), the OGR/WVR components of the formulation can prolong the useful life of the product on the skin. For example, adding OGR/WVR formulations to the NCE matrix bearing the active agent is useful for those topical applications (whether for medical or cosmetic purposes) for which an enduring period of skin contact is desirable. OGR/WGR formulations can also be added to those compositions used for transdermal patches to protect the patches from water, perspiration, skin oils, and the like that might otherwise loosen the patches and interfere with the delivery of their active agents.

NCE vehicles applied to the skin can be used for other applications, such as semipermanent tattooing, or the application of conductive lines or shapes to the skin to interface with sensors to communicate information (for example, as RFID tokens for wireless pay, portable medical records, biometrics, health monitoring, etc.). Other NCE-based formulations can be used for specialty inks, paints, adhesives, or conductive coatings or conductive elements, where the NCE matrix provides support for the active agents or active particulate matter.

In an advantageous embodiment, lignin or other specialty substances such as melanin or other dyes or pigments can be incorporated into matrices formed from suspended NCEs to produce pigmented formulations for use in hair, nails, fabrics, and the like. The natural affinity of NCEs with the skin can support the development of nail formulations with pigments or other aesthetic elements within the NCE matrix to provide a strong and chip-resistant nail polish for cosmetic uses, or to treat fragile or damaged nails, without requiring varnishes or harsh organic solvents. In other embodiments, NCEs can be used as strengthening agents for conventional nail polishes to improve their strength and chip resistance, or to treat fragile or damaged nails.

In embodiments, a NCE matrix can be shaped to provide the structural and architectural features for a particular article of manufacture. As an example, a foamed NCE matrix, optionally combined with materials such as hydroxyapatite, can provide a strong bone graft that can act as a scaffold for osteoblasts to inhabit to produce bone tissue. Alternatively, the NCE matrix can be shaped as a solid bone graft without foaming but with the inclusion of other strengthening and/or bone-forming substances within the matrix. In embodiments, NCE can also be used as a scaffold for biomaterials that are not intended to degrade quickly, such as surgical meshes, semi-permanent sutures, or scaffolds for bioengineered implants, due to the durability of NCEs within the body. In embodiments, the NCE substance can be engineered to have more or less biological durability, depending on the envisioned application. In embodiments, the NCE matrix can also be formed as threads, elongated fibers, and the like, for specialty applications. As an example, spun threads formed from the NCE matrix can be used alone or with integrated protein materials such as collagen as dissolving suture materials or biocompatible meshes, with customizable rates of decomposition and customizable strength engineered into the materials for specific uses.

b. NCEs as Additives in Composite Materials: General Characteristics

In embodiments, a population of NCEs can be incorporated into an existing matrix composition (termed an "existing matrix"), for example organic matrices such as paper matrices, plastic matrices, liquid resin matrices, wood-based composites like TREX, and inorganic matrices such as cement and plaster. Such matrices, formed with a redispersed or redispersible population of NCEs incorporated into an existing matrix is termed a "composite matrix." In more detail, NCEs to be incorporated in an existing matrix to form the composite matrices can be provided as redispersible, dried NC-containing material with NC elements embedded therein as described herein, or they can be provided as NC elements that have been redispersed and suspended in a redispersing formulation, as described herein. In either case, NCEs so prepared and provided are termed "additive NCEs" with reference to their inclusion in a composite matrix. Composite matrices therefore are understood to be combinations of additive NCEs and existing matrix compositions.

In embodiments, the matrix-forming substances are coated with and/or impregnated with additive NCEs to form the composite materials. As a result, the composite materials can be equipped with specialized properties that exceed those found in the original matrix-forming substance, or that are not found in the original matrix-forming substance. For example, the composite material can exhibit a specialized intrinsic mechanical property such as strength, hardness, toughness, brittleness, stiffness, cohesion, durability, impact resistance, optical transparency, and the like, where such a property exists in the original matrix-forming substance but where the presence of the NCEs in the composite article improves that specialized property. As another example, the composite material can exhibit a barrier property such as a hydrophobic, oleophobic, or water-resistant property that can be present in the original matrix-forming substance but is improved in the composite material, or that is absent in the original matrix-forming substance but is provided in the composite material. As yet another example, the composite material can exhibit an adscititious property, i.e., a property that is not present in the original matrix-forming material but that is produced through the use of the NCEs in their ordinary or modified state. Such an adscititious specialized property, i.e., typically absent in the original matrix-forming material but imported via the incorporation of a NCE formulation in the composite material, is electrical conductivity, which can be introduced into the composite material through the use of NCEs and the silver mirror effect and the like, as discussed below in more detail.

Specialized properties of composite materials using NCEs have already been contemplated in industry, but their use has been hampered by the redispersion problems mentioned previously. The redispersion technologies disclosed herein facilitate the transportation of NCE compositions that can then be resuspended to be combined with other matrix-forming materials, yielding composite materials. In embodiments, these redispersion technologies can produce a uniform mixture of high-aspect-ratio NCEs within the primary matrix-forming material, allowing enhancement of desirable specialized properties in the final composite, including intrinsic mechanical properties such as strength, hardness, toughness, brittleness, stiffness, cohesion, durability, impact resistance, optical transparency, and the like, as described above in more detail. In other embodiments, the use of NCE formulations produced using the redispersion technologies disclosed herein can introduce or enhance specialized properties such as barrier properties that allow the composite to have desirable degrees of oil and grease resistance and/or water vapor resistance. In yet other embodiments, the use of NCE formulations produced using the redispersion technologies disclosed herein can provide the composite material with a new specialized property such as electrical conductivity that is not present in the original matrix-forming material.

i. NCEs as Fillers: Exemplary Articles

Fillers are understood to improve mechanical properties of organic and in organic substances, or make the product cheaper, more lightweight, and the like. Fillers can improve composite properties such as strength, hardness, toughness, brittleness, stiffness, cohesion, durability, impact resistance, optical transparency, and the like. While NCEs have already been used as fillers in consumer products, their use has been limited due to redispersibility problems described herein. The methods for NCE redispersion as disclosed herein can permit the more widespread adoption of these additives as reinforcing agents for paper, resin, cement and plastic, and can further permit a dramatic expansion of new uses. As used herein, the term "reinforce" refers to an improvement of an mechanical characteristic pertaining to strength, hardness, toughness, brittleness, stiffness, cohesion, durability, impact resistance, optical transparency, and the like, that is found in the existing matrix; a composite matrix having improved mechanical properties as compared to the constitutive existing matrix can be termed "reinforced," with the reinforcement of the composite material attributable to the presence of the NCEs.

NCEs, although intrinsically hydrophilic, can be employed as fillers within a hydrophobic environment as well. For use in a hydrophobic environment, the NCEs can be surface-modified to match the properties of the hydrophobic matrix in which they are to be incorporated, so that they are compatible with the matrix and can be evenly dispersed within it. In embodiments, surface modification of additive NCEs prepared in accordance with the methods disclosed herein can be performed, for example using a hydrophobic monolayer on the NCEs. Such NCEs that have been hydrophobized for use in hydrophobic matrices are not only redispersible upon drying (like unmodified NCEs in a hydrophilic environment) but also, by virtue of their hydrophobic coating, they are compatible with various polymeric, "plastic" matrices, such as thermoplastic and thermoset matrices (e.g., polypropylene, polyethylene, polystyrene, polyesters, poly(acrylates/methacrylates), rubbers, silicones, urethanes, epoxies, and the like, to yield strong and lightweight non-porous solids for molding or extrusion, and open-cell or closed-cell foams for other applications. In embodiments, hydrophobically-modified NCEs can offer renewable, lightweight, high-performance fillers for advanced composite hydrophobic materials, for uses such as vinyl siding, decking flooring, composite roofing, injection-molded plastic parts, automobile bumpers, fenders and dashboards, reinforced Styrofoam products such as insulation blocks and ceiling tiles, and the like. In other embodiments, NCEs can be dispersed within adhesives that are generally added to matrix materials such as oriented strand board or other wood-based building materials, thereby improving the strength of the adhesive itself and the strength of the matrix materials.

The lightweight and environmentally friendly nature of NCE reinforcing fillers is especially suitable for medical uses, in which NCEs can be used to add strength to medical articles, such as may be intended for temporary use. For example, NCEs can be added to cast material to strengthen it without adding weight. As another example, NCEs can be added to bandage materials to strengthen them. When incorporated in a conventional bandage or a hydrogel bandage, NCEs make the bandage more durable while adding some structural protection to the healing wound. Similarly, NCEs can provide reinforcement when used in cosmetic products. Patches bearing pharmaceutical, nutraceutical, or cosmetic active agents can obtain significant strength enhancement with low doses of NCEs dispersed through the product. NCE fillers can be used with conventional polymeric matrices such as hydrogels, polyethylene, PVC, and other dressing materials, allowing improved strength and durability while permitting lighter and thinner bandages. NCE fillers can also be used with NCE matrices, as discussed previously, to improve strength and durability. Similarly, cosmetic products such as face masks, nose strips, and acrylic (faux) nails can benefit from the adhesive and strength imparting properties of NCE fillers.

As another example, NCEs incorporated into other polymeric matrices as fillers can offer an environmentally attractive option for strengthening recreational equipment articles. In embodiments, an NCE-strengthened polymer can serve as a substitute for the synthetic materials used in surfboards and boat hulls (such as fiberglass resins, polyurethane or polystyrene foam cores (surfboards), carbon fiber, fiberglass, polyethylene (sculls)), retaining strength with less weight, and in a more environmentally conscious manner. NCE additives can also be used to improve strength and elasticity in recycled plastics. They can also facilitate the transition from petroleum sources of plastic materials to more sustainable sources of plastics, which often lack the performance characteristics of the petroleum-based materials. For example, Lego has experimented with using biopolyethylene derived from sugar cane, but may be unable to use this material as a substitute for the petroleum-based acrylonitrile-butadiene-styrene (ABS) copolymer that is used to form its bricks; NCE additives can improving the toughness and strength of materials like biopolyethylene, allowing the reinforced, bio-derived composites to be used as potential replacements for materials like ABS.

As yet another example, for athletic shoes, soles can be made from NCE-strengthened polymers or as composites using NCE matrices, in order to reduce the amount of materials such as ethyl vinyl acetate and polyurethane and silicone gels used in the shoes, thus offering a more environmentally friendly product. NCE matrix foams or foams containing NCE reinforcing fillers can be used in these applications, providing support and comfort for the wearer. This inclusion of NCEs can increase the bend-twist-tear resistance through the strengthening effect of the fibers while also keeping the sole of the shoe lightweight and shape-holding. As an added benefit, viscoelastic dampening can be imparted by the matrix of fibers throughout the sole, interrupting the transfer of physical shockwaves through the sole and into the wearer's body with small, rigid fibers to absorb parts of the physical force.

As a further example, architectural paint products containing resuspended NCEs can be formulated to be inherently primed, allowing immediate use on drywall, wood, concrete, brick, and the like. The presence of the NCEs in the paint product can provide improved substrate adhesion and drip suppression, crack resistance, and resistance to corrosion. Other opportunities exist for improving construction materials by incorporating NCEs, for example, to produce high-performance materials such as sag-free stucco, lightweight and strong sheetrock (dry wall), oriented strand board and similar composites, faux-wood-concrete countertops that have are easy to process and crack-resistant, synthetic flooring and bath tiles, plaster moldings, joint compounds, artificial-lightweight sculpted stones, recycled-glass-cement-NFC/MFC composites, and the like. Opportunities to create durable inks that can be used on compostable products also exist through the use of NCE-filled resin. Wheeled vehicles, such as automobiles, trucks, aircraft, ATVs, motorcycles, scooters, bicycles, wheelchairs, and the like, can also benefit from NCE-filled tires to improve wear resistance, strength, and durability. Lightweight, foamed versions of NCE-containing materials can be formed for specific applications.

NCEs can be used as fillers in a variety of environments, as the foregoing examples demonstrate. Once redispersed, the NCEs can be provided with an appropriate coating to enable them to interact with the selected polymeric matrix. They can thus add strength and elasticity without weight to composite materials that incorporate them. They can also substitute for existing fillers in order to provide a plant-derived alternative to conventional petroleum-derived or inorganic fillers. For example, 3D printing materials are typically plastics like ABS, polylactic acid, polyvinyl alcohol, polyethylene terephthalate glycol, nylons, and a variety of resins, which can be reinforced with fillers like carbon fibers, Kevlar, fiberglass and the like. NCEs can be substituted for the inorganic fibers as more sustainable components of the overall 3D printing substrate.

ii. NCEs as Matrix Pore-Closers: Exemplary Articles

The nano-dimensions of NCEs enable them to be incorporated within the pores of existing matrices to produce advantageous properties for the resulting composite article, where their advantageous properties are based on their presence within the pores to decrease the porosity of the native matrix. In embodiments, NCEs can thus be used as a coating product for existing matrices, like paper products, to fill the pores in the paper matrix to create high-value, specialty paper products. As an example, a paper product with NCEs embedded in its pores can offer oil and grease resistance. As another example, a paper product with embedded NCEs in its pores can be engineered to form a releasable label backing or selective adhesive. In embodiments, all forms of cellulose, hydrophobic emulsions, fatty acids, any film-forming material, etc., can be used for these sorts of applications, where NCE-based formulations are used to provide advantageous properties in composite articles. All such additives can be used alone as a single additive, added together, or added sequentially.

iii. NCEs as Substrate Components: Exemplary Articles

While films, sheets, formed articles, and the like, can be formed substantially entirely from NCE matrices, as described above additive NCEs can be integrated into existing matrices made from other polymeric materials to produce composites having advantageous and/or specialized properties. Such existing polymeric matrices receptive to the addition of additive NCEs prepared by the methods disclosed herein can be provided as formulations suitable for the incorporation of the additive NCEs, and optionally including other additives having advantageous properties. By selection of appropriate polymers and additives for the existing matrix within which NCEs are integrated to form a composite material, properties such as structural strength, resilience, elasticity, water resistance, oil and grease resistance, and the like, can be imparted to useful articles formed therefrom, in combination with biodegradability. These polymeric matrices and formulations to which additive NCEs are added in order to produce composite matrices are termed "constitutive polymer substrates (CPS)."

In embodiments, addition of NFC/MFC to a CPS can be done directly from low concentration suspensions (~2 wt %) or may be added in dried form with redispersion additives to cut down on water, cost, and to enhance redispersion. The final NCE-containing polymer formulation can be prepared at high concentrations for extrusion processes on an industrial scale. The extruded films can then be dried and/or molded into their final geometries (for bags, lids, containers, films, etc.). Illustrative examples are provided below.

(a) Example: Films and Sheets

As an example, films used as wrappers for food products can be made using a combination of conventional biodegradable, naturally derived materials such as cellulose ethers, cellulose esters, starch ethers, starch esters, polyvinyl alcohol, hydroxyethyl butyrate, or any combination thereof, with NCE and dispersant additives as described above incorporated to impart intrinsic mechanical properties to the films, including without limitation, improved mechanical strength for tear resistance and rigidity. In embodiments, the NCE additives can be fibers coated with films to provide oil and grease resistance and/or water resistance. Cellulose acetate, or other hydrophobic, stretchy materials, can be added to impart elasticity onto the coated fibers, or can be incorporated into the polymer matrix to provide flexibility and stretchiness for the products. For products that require gas-barrier properties, polyvinyl alcohol or copolymers of polyvinyl acetate/polyvinyl alcohol are advantageous.

Composite films or sheets incorporating NCEs can be transparent or translucent as desired, with superior mechanical properties such as tear resistance, along with biodegradability. By contrast, plastic films and sheets, such as are used for Ziplock bags, garbage bags, grocery bags, and the like, are typically formed from polyolefins such as polyethylene and polypropylene, which are petroleum-derived and slow to degrade. In embodiments, films and sheets formed by incorporating NCEs as described herein can be used for a multitude of other packaging applications where strength is desirable, to provide a biodegradable alternative to conventional polyolefin-based packaging materials. Such films and sheets can also be formed with barrier properties (e.g., OGR or WVR or both), using the techniques disclosed herein. Such a composite, comprising NCEs prepared according to the methods disclosed herein and having barrier properties, is termed a barrier material. Barrier materials can advantageously be formed as films, sheets, containers, or other articles of manufacture in which designated barrier properties are desired.

In more detail, in embodiments, a barrier material can be prepared from a base formulation of biodegradable materials such as cellulose ethers, cellulose esters, starch ethers, starch esters, polyvinyl alcohol, hydroxyethyl butyrate, polyvinyl acetate, or any combination thereof, with additives to impart specific properties to meet a particular need. For example, for a barrier material requiring gas-barrier properties can include polyvinyl alcohol, polyvinyl acetate, copolymers thereof, and blends thereof. For water and oil repellency, methyl cellulose is a desirable additive. To improve mechanical strength, NCEs can be added at concentrations ranging from 1 wt % to 10 wt %. In embodiments, a base formulation can be prepared with polymers with molecular weights ranging from tens of thousands g/mol to millions g/mol, with the specific polymer(s) selected for optimal physical integrity; advantageously, high molecular weight versions can be selected (for example, in molecular weight ranges from a hundred thousand g/mol to millions g/mol). Addition of plasticizers may be incorporated at concentrations ranging from, for example, about 1 wt % to about 50 wt %, or about 1 wt % to about 10 wt %, or about 5% to about 15%, to impart flexibility. Plasticizers can include, but are not limited to 1,2-propanediaol, xylitol, erythritol, maltitol, and mannitol, or fatty acids such as caprylic acid, caproic acid, or the like. Fatty acids used as plasticizers may be beneficial in a barrier application due to its hydrophobic nature. Addition of NCEs can be done directly from low concentration suspensions (~2 wt %), or can be added in dried form and redispersed using the redispersing agents as described herein. For large-scale processing, the full formulation (including redispersion polymer(s), NFC/MFC, plasticizers, and desired additives) can be mixed in a large tank and pumped to an extruder with a slit die. Extruded sheets may then be pressed and/or perforated with rollers. After drying (heated rollers or ovens) the pressed sheets can be collected into rolls or further shaped into bags or sachets.

An exemplary formulation to produce wrappers or containers or sachets for non-oxygen sensitive substances (e.g., salt/pepper) can include the following ingredients (by weight, based on a total formulation weight of 100 g):

Methyl cellulose (MC): 85.5 g
Xylitol: 4.5 g
NCE: 10 g

An exemplary formulation to produce wrappers or containers for oxygen-sensitive materials (e.g., see-through films for meat trays) can include the following ingredients (by weight, based on a total formulation weight of 100 g):

Polyvinyl alcohol (PVA): 23.75 g
Polyvinyl acetate (PVAc): 23.75 g
Methyl cellulose (MC): 42.75 g
Maltitol: 4.75
NCE: 5 g (b) Example: Fibers and Nonwoven Fabrics In embodiments, the formulae used to produce films and sheets reinforced with NCEs can be used to create other useful shapes or forms, such as threads and fibers. The formulae previously described can be used in combination with NCEs as the composite substrate material that can be formed into strong, biodegradable fibers that can be used for many applications, such as (without limitation) healthcare specialty products (sutures, meshes, implantable drug dispensing vehicles, and the like), nonwoven materials (wipes, coffee filters, tea bags, cloths, dryer sheets, and the like), and fibrous reinforcers for building or packaging materials to add strength, shock absorbency, and resiliency.

As described previously, an NCE matrix useful for these purposes can be formed as an NCE material alone. However, this section exemplifies producing a composite material incorporating NCEs in a polymeric matrix made from other, non-NCE substances. For example, a composite material can be formed as previously described, using a natural, biodegradable polymers as disclosed herein to form the CPS, to which NCEs can be added to improve strength, toughness, brittleness, stiffness, cohesion, durability, impact resistance, and the like. The CPS can also incorporate other secondary additives to impart advantageous specialized properties to the overall composition, such as mechanical properties, barrier properties (e.g., hydrophobicity/hydrophilicity, oil and grease resistance, and the like) and adscititious properties (e.g., electrical conductivity, elasticity, malleability, and the like). The final CPS, with all desired additives and with the NCE inclusions, can then be formed into a variety of useful articles.

In embodiments, the composite described above can be formed into fibers or non-woven materials. As a first step, a CPS, for example a viscous polymer formulation comprising one or more biodegradable polymers, is prepared. Biodegradable polymers that can be used in the CPS for this purpose include such polymers as polyvinyl alcohol that is fully or partially hydrolyzed, polyvinyl acetate, cellulose derivatives (cellulose ethers and esters, such as methylcellulose (MC), hydroxyethyl cellulose (HEC), hydroxypropyl cellulose (HPC), hydroxypropylmethyl cellulose (HPMC) and the like), polylactic acid, polygalactic acid, polyhydroxybutyrate, polyvinylpyrrolidone, and mixtures thereof. Polyvinyl alcohol is advantageous for certain applications due to its oxygen impermeability. Other natural polymers that can be used in the CPS include chitosan, zein, pectin, and natural proteins (soy, whey, pea, and the like).

NCEs can be added into the CPS to impart specialized properties, including intrinsic mechanical properties, barrier properties, and adscititious properties. A desirable specialized property is an intrinsic mechanical property such as extra strength, hardness, toughness, brittleness, stiffness, cohesion, durability, impact resistance, or a selected optical property such as transparence, translucence, and the like. Once included in the CPS, the NCEs can remain deployed as fibers and can align with themselves in a straight or randomly oriented way, to form networks or other internal architecture within the CPS. In embodiments, an amount of NCEs in the final substrate can range from about 1 wt % to about 30 wt %.

Before or after the addition of the NCEs to the CPS, certain of the formulation's specialized properties can be optimized. In embodiments, the optimized specialized property is a mechanical property. In embodiments, the optimized specialized property is a barrier property. In embodiments, the optimized specialized property is an adscititious property. The optimization of the CPS can result in a formed article or article of manufacture, such as fibers or non-woven fabrics, having optimized specialized properties.

As an example, the hydrophobicity/hydrophilicity of the CPS can be adjusted, depending upon the final application, by the addition of substances selected to impart those desired properties such as increased strength or tuned hydrophobicity/hydrophilicity. For a more hydrophilic fiber, biodegradable gums or other hydrocolloids can used in conjunction with or to replace the biodegradable polymers mentioned above, for example adding xanthan gum to the CPS or replacing certain of the constitutive polymers in the CPS with xanthan gum. For a more hydrophobic fiber, biodegradable polymers that are more hydrophobic, such as methylcellulose, may be used; in addition or alternatively, to impart additional hydrophobicity, small amounts of very hydrophobic materials, such as waxes, oils, or emulsions thereof, can be added. If waxes are added, the CPS can tend to form an emulsion instead of a suspension, in which case surfactants such as fatty acids or others can be used to enhance the incorporation of the waxes into the overall CPS.

After a CPS has been formulated to incorporate the NCEs and any desirable secondary additives, it provides a viscous substrate for further shaping, for example for forming fibers. Optionally, glycerol, or other small molecules that interact with the constitutive polymer chains or that insert themselves in between them can be added to the substrate to act as plasticizers, which can result in the formation of a less brittle, more malleable fiber once shaped. Plasticizers that can be used including without limitation such previously mentioned substances as glycerol, propanediol, erythritol, xylitol, mannitol, maltitol, sorbitol, and the like, as well as fatty acids such as stearic acid, palmitic acid, myristic acid, lauric acid, capric acid, caprylic acid, caproic acid, and the like.

After the composite matrix (i.e., the suspension of the NCEs in a constitutive polymer formulation, with appropriate secondary additives) has been formulated, it can be shaped using techniques familiar in the art for processing viscous or melted substrates to form fibers. In more detail, the substrate can be prepared at a suitable viscosity so that it can be directed through an extruder or a spinneret system. The substrate's viscosity can be adjusted by adding more or less water to it, by incorporating secondary additives, including thinning or thickening agents, by changing its temperature, or by other mechanisms familiar in the art.

Once the composite matrix has attained a suitable viscosity, it serves as an amorphous substrate that can be forced through an extruder or a spinneret, i.e., a die comprising a number of holes or channels. Passage of the amorphous substrate through the extruder or the spinneret holes results in the elongation of the substrate to form one or more fibers. As would be understood by skilled artisans, the number of holes in a spinneret can produce a defined number of fibers that can be entwined with each other in a subsequent step to form a yarn or a thread. As would also be understood by skilled artisans, a single-hole extruder can be used to form a continuous single fiber or thread, which can subsequently be divided mechanically into smaller fibrils, for example by cutting the single fiber longitudinally or transversely. In embodiments, the NCE fibrils can align directionally within the single or multiple extruded polymeric fibers to enhance their resistance to transverse or longitudinal stress.

Following the extrusion process, the fibers can pass through a region to solidify the fibers for their intended uses. For example, if the fibers had been derived from a heated substrate and they still retain heat after extrusion, they can be cooled to the temperature of their intended use or re-heated as necessary, e.g., to drive off excess water. Or, for example, if the extruded fibers are still excessively pliant or stretchable, they can be hardened by exposure to a coagulant bath to crosslink some of the component polymers, or to an air gap that drives off volatile components of the substrate and allows subsequent coagulation. Following the optimization of the extruded fibers, they can be combined to form a yarn or a thread, which can then be further treated with a spinfinish as needed, in keeping with techniques familiar to skilled artisans. The yarn or thread can be further processed using one or more godet rolls running at appropriate speeds and temperatures in order to align the polymeric materials with each other and with the NCEs within the fibers and to eliminate voids within the fibers, thereby making the material stronger. In embodiments, fibers or filaments made from biodegradable, NCE-containing CPS substrates as disclosed herein can be used for a number of applications.

In embodiments, these NCE-containing products can be used to form biodegradable non-woven materials, advantageously providing an alternative to conventional nonwovens that are made from non-biodegradable materials like polypropylene or polyester. It is understood that nonwoven fabric can be formed from fibers or filaments that are attached together in a random pattern to form mats, without the need of converting the fibers or filaments into yarns or braided threads. The formation of nonwoven fabrics is thus distinctive from traditional weaving, knitting, or braiding techniques for forming fibers or filaments into fabrics. Two major processes are involved in forming nonwoven fabrics: web formation and web consolidation. Using these techniques with fibers or filaments produced from NCE-containing CPS substrates can yield biodegradable nonwoven materials having advantageous properties.

Web formation processes for producing such biodegradable materials would subject the fibers and filaments produced as described above to such techniques as carding, air laying, wet laying, spun-bonding, melt-blowing and more recently electro-spinning, as would be understood by skilled artisans. Web consolidation processes for producing such biodegradable materials can include such techniques as needle-punching, spunlacing, chemical bonding, and thermal bonding.

Fibers or nonwoven materials formed from NCE-containing CPS substrates can produce fibers or fabrics that exhibit optimized properties such as fabric handling and drapability, tensile properties, abrasion resistance, pilling and washing stability, dyeing and printing adaptability, and other features that permit these biodegradable materials to be used for a variety of applications. In embodiments, the product formed from these biodegradable materials is customized so that it retains sufficient integrity and strength for its desired purpose, while being susceptible to biodegradability after it is discarded. Examples include, without limitation, products such as cleaning towels (analogous to microfiber cleaning cloths), wipes, absorbent materials, tea bags, coffee filters and similar food-related filters, filters for industrial and consumer use including HEPA filters, vacuum bags, and medical gowns, drapes, covers, masks, bandages and other wound dressings, and packaging systems, in addition to the aforesaid dryer sheets and similar products.

As another example, artificial fabrics and fibers that are NCE-derived can be formed to produce an artificial leather. Conventional artificial leather is made by taking artificial fabric, such as polyester, and soaking/coating it in polyurethane, polyvinyl chloride, or wax. These products have poor performance vs natural leather, and they are made from synthetic, non-biodegradable plastic materials. As an alternative, a naturally-derived artificial leather can be made using fibers or fabrics made from NCEs. As described above, NCE-based fabrics can be produced that form the basic substrate for the artificial leather, while reinforcement can be added from fibers spun from NCEs or added from NCEs themselves acting as filler particles (or both). OGR/WVR coatings can be added to the fibers, using the techniques described above. Cellulose acetate, or other hydrophobic, stretchy materials, can be added to impart elasticity onto the coated fibers and therefore the final leather product. The addition of strength from NFCs/MFCs, as well as the elasticity from the cellulose acetate can create a durable, naturally derived leather alternative. Hydrophobic plasticizers, such as triacetin or citrate esters, fatty acids etc., can be used to impart elasticity as well.

(c) Example: Drinking Straws

An application combining the features of biodegradability, strength, and barrier properties is the use of NCE materials to form an article of manufacture formed as a biodegradable drinking straw. Because straws are intended to be used with a variety of liquids, including alcohol, fats, acids, and the like, at various temperatures, and because straws require sufficient strength to resist deformation during normal use, there has been a tendency to use more durable plastics that are not biodegradable; biodegradable materials alone lack the liquid tolerance and strength to withstand the stresses that straws typically encounter. The use of NCE materials alone or in combination with other biodegradable materials can provide the necessary liquid tolerance and strength, while permitting the product to be biodegradable. As described previously, the NCE matrix alone can be formed as a sheet and rolled into a hollow cylinder to act as a straw. In other embodiments, a composite material can be formed, for example using a derivatized cellulose such as methylcellulose combined with NCEs, where the methylcellulose or analogous biodegradable LCST polymers or other materials like cellulose acetate, lipids, polyvinyl alcohol or copolymers of polyvinyl acetate/polyvinyl alcohol, waxes, wax emulsions hydrophobic starch, fatty acids, or other hydrophobic cellulosic polymers, or any other similar hydrophobic polymers can increase the hydrophobicity of the material.

In an embodiment, methylcellulose (MC), cellulose acetate, lipids, polyvinyl alcohol or copolymers of polyvinyl acetate/polyvinyl alcohol, waxes, wax emulsions hydrophobic starch, fatty acids, or other hydrophobic cellulosic polymers, or any other similar hydrophobic polymers in dry form can be combined with dried, redispersible NCEs that have been pretreated with a redispersion additive, such as a combination of a small molecule plasticizer and a biodegradable polymer such as a cellulosic polymer as described above, with the MC and NCE mixture being ground into powder form. The powdered mixture can then be stirred into water to create a viscous mixture that can then be formed as a sheet or extruded as a hollow cylinder. In embodiments, a ratio of the redispersion additive (e.g., small molecule and biodegradable polymer) to the NCE elements can be in a range from about 1:1 to about 15:1, or in a range from about 3:1 to about 12;1, or at a ratio of about 6:1 with a variety of balances between the biodegradable cellulosic polymer and the small molecule plasticizer available, for example a 70/30 balance of polymer to small molecule, or a 50/50 balance between polymer and small molecule, or a 0/100 balance between polymer and small molecule, or any balance of the two components in between the exemplary ratios provided. For embodiments engineered to have barrier properties, the ratio of OGR or WVR ingredients to NCEs can be from about 1:1 to about 12:1, or between about 3:1 to about 9:1. In another embodiment, a 2-3% suspension of NCEs can be mixed with a MC or other cellulosic-containing suspension. In embodiments, the NCE formulation can comprise CMFs as well as CNFs, or can comprise more CMFs than CNFs, or can be consist essentially of CMFs, with the CMF to CNF ratio being adjusted to optimize the strength of the final formulation. In embodiments, regular pulp can be used in addition to or instead of derivatized cellulose in the mixture. Eliminating or decreasing the amount of the glycerol or other plasticizer used in the formulation can improve the stiffness of the straw product. Spun hydrogel fibers can be added to the composite to improve strength and flexibility.

(d) Example: Biodegradable Alternatives to Conventional Products

As described previously, composite matrices as disclosed herein offer biodegradable alternatives to conventional products.

For NCE/starch composites, cellulose microfibers are advantageous, either alone or in combination with cellulose nanofibers, as additives to the starch-based CPS. Foaming can be produced by mechanical means, or by incorporating foam-forming elements such as surfactants in the mixture. Bicarbonate crystals can also be incorporated into the mixture as a foam forming element with a later addition of acid to activate foaming. Secondary additives such as linseed oil or more hydrophobic cellulose additives, such as methyl cellulose, cellulose acetate, lipids, polyvinyl alcohol or copolymers of polyvinyl acetate/polyvinyl alcohol, waxes, wax emulsions hydrophobic starch, fatty acids, other hydrophobic cellulosic polymers, or any other similar hydrophobic polymers can be added to improve hydrophobicity; alternatively or in addition, the NCE additives can be prepared having OGR properties.

In embodiments, a composite matrix produced using biodegradable materials as the existing matrix can be used to produce foams and foamed articles. Conventional foamed products made from biodegradable materials, for example foams formed from starches, typically have poor performance relative to petroleum-derived foams, often lacking the strength and hydrophobicity of petroleum-derived products. NCE-based foams, derived predominantly from NCE matrices can act as substitutes for conventional foams for uses such as packing materials, as described above. Composite materials, comprising mixtures of NCEs and biodegradable materials such as starches or derivatized cellulose (e.g., cellulose ethers or cellulose acetate), can also be prepared as foamed articles and can be similarly used as substitutes for conventional foams, combining the advantages of biodegradability with the desirable strength, shock absorbency, light weight, and water resistance that packing materials and containers require.

In embodiments, redispersed or redispersible NCE additives prepared according to the techniques disclosed herein, can be used as carriers to impart barrier properties onto biodegradable existing matrices such as those formed from pulp or pulp-based materials. To do this, NCEs can first be treated in the same way as previously described to allow for redispersability. A cellulosic polymer mixed with a plasticizer can be added to an as-received 2-3% NCE slurry, and it can be dried into a sheet or into any other form or shape. Once dry, the product then can be ground up into small particles resembling a powder. To this new powder, one or more hydrophobic or oleophobic materials can be added in order to impart barrier properties. This barrier-producing material can advantageously be somewhat soluble or solubilizable in water to facilitate handling, for example a hydrophobic starch, a cellulosic polymer that is more hydrophobic, such as methyl cellulosic, or a fatty acid. The barrier-producing material can be added in ratios ranging from 1:1 barrier additive to NCE to 15:1 barrier additive to NCE, and preferably from 3:1 to 9:1. The barrier-producing material can also be an oil-in-water emulsion or a wax emulsion. A secondary additive such as a plasticizer can be added in this step as well. The composition that is produced is either a powder or paste material that can be shipped in its concentrated form and later dissolved into water to be added to a selected, biodegradable existing matrix to produce a composite matrix having barrier properties. For example, the slurry of ingredients can be used as a mix-in barrier additive for pulp-molded or pulp-based products as described previously, or it can be used as a coating for an already-made pulp or pulp-based product, as described previously. It can also be used to impart barrier properties to fibers: the composite matrix including the barrier treatment can be molded into a product, extruded to form fibers, spun into fibers, or otherwise processed to yield a composition or formed article possessing barrier properties. The composition or formed article is then dried, allowing it to display the barrier properties in dried form.

In embodiments, composite matrices can be produced from biodegradable existing matrices having combinations of specialized properties, such as advantageous mechanical properties and barrier properties. As an example, packing materials can be formed from natural polymeric materials as described previously, such as starch or derivatized cellulose (cellulose ethers or cellulose acetate), with optionally added barrier polymers or optionally added barrier-treated NCE foam, wherein the natural polymeric materials are reinforced with NCE-reinforced fibers. In an embodiment, natural polymeric materials can be spun into threads or fibers, with the NCE strands aligning within the spun fiber to create a strong, reinforced fiber. A foamed product such as a packing peanut made of previously described natural material can be reinforced with these NCE-reinforced polymer fibers to form a packaging material that is a lightweight network with shock absorbing properties. Small fibers or bunched-up balls of longer reinforced fibers can be used as reinforcement in the overall packing material matrix for increased shock absorbency. NCE strands for this purpose can have intrinsic hydrophobicity, and optionally can be treated with materials to improve their oil and grease resistance. Overall, these natural materials and NCE reinforcements (NCE fibers and/or NCE-reinforced polymer fibers) can be used for many packaging applications, including in packing peanuts, bladders, cardboard boxes, etc.

(e) Example: Conductive Materials

In embodiments, the additive NCE population can include a subpopulation of NCEs that are modified via the silver mirror reaction to allow their use in conductive applications.

The silver mirror reaction produces a metallic silver layer on a surface as a result of a redox reaction by the interaction of an ammonia complex of silver and an aldehyde. The first stage of the silver mirror reaction, using Tollen's reagent (an ammonia solution of silver oxide), is set forth in the following equation, EQ.1:

$$Ag_2O + 4\ NH_3 \cdot H_2O \leftrightarrows 2[Ag(NH_3)_2]OH + 3H_2O \qquad EQ.1$$

where [Ag(NH$_3$)$_2$] is silver diamine hydroxide, produced by the metal oxide dissolving in the ammonia solution.

The second stage of the silver mirror reaction, showing the reaction of silver diamine hydroxide and an aldehyde R—CH═O, is set forth in the following equation, EQ.2:

$$R\text{—}CH\text{═}O + 2[Ag(NH_3)_2]OH \rightarrow 2Ag\downarrow + R\text{—}COONH_4 + 3NH_3 + H_2O \qquad EQ.2$$

where [Ag(NH$_3$)$_2$] is silver diamine hydroxide, produced by the metal oxide dissolving in the ammonia solution, and where the products include a carbonic acid amine, an ammonia solution, and a silver precipitate that forms the "silver mirror."

If a subpopulation of NCEs, whether NFCs, MFCs, or mixtures thereof, are soaked with an aldehyde so that the aldehyde groups are presented on the surface of the NCEs, the redox reaction will occur on that the surfaces of these NCEs. Aldehydes useful in this reaction can include glutaraldehyde, cinnamaldehyde, vanillin, or the like. These aldehyde-bearing NCEs can then be exposed to an ammonia complex of silver, resulting in the deposition of a silver sediment on the surface of the NCEs. As a result, a conductive and reflective coating can be deposited on the NCE subpopulation. If this subpopulation is included in a composite matrix prepared as disclosed herein, the composite matrix will have conductive properties, allowing it to be used in conductive and/or reflective applications. As examples, conductive and highly reflective NCEs can be used in applications where a combination of strength and conductivity are advantageous, for example, in fitness, health care and medical industries, as well as in cable cladding, EMI shielding, circuit board manufacturing, and overall electrode construction. Other applications in which the elongated structure, high surface area, and ability to be dispersed and coated offer advantages would be apparent to those of ordinary skill in the relevant arts.

EXAMPLES

Materials used in Examples 1-4 include:
NFC suspensions in water (obtained from various sources, including Performance Biofilaments, SAPPI, University of Maine, and Auburn University)
Chemicals (all obtained from Sigma Aldrich unless otherwise designated)
Tri(propylene glycol) butyl ether (TPnB)
Di(propylene glycol) propyl ether (DPnP)
Propylene glycol butyl ether (PnB)
Propylene glycol propyl ether (PnP)
Butylene glycol ethyl ether
Ethylene glycol monobutyl ether (2-butoxyethanol)
Propylene glycol monomethyl ether acetate
Propylene glycol diacetate
Ethylene glycol diacetate
Benzyl alcohol
1-heptanol
1-hexanol
Caffeine
Glycerol
Piperazine
Pyridine
Methylcellulose (MC)
Hydroxyethyl cellulose (HEC)
Hydroxypropyl cellulose (HPC)
Hydroxypropylmethyl cellulose (HPMC)
Poly(methyl vinyl ether)
Melamine
Triethanolamine
Dytek EP (1,3 diaminopentane)
Ethylenediamine
Diethylenetriamine
Tetraethylenepentamine
1,2-Diaminocyclohexane
Polyethyleneimine (PEI)
Ethylenediaminetetraacetic Acid (EDTA)
Luviskol Plus (polyvinylcaprolactam) (BASF)
Corning stir plate
BINDER forced convection oven Example 1: Direct Additive Application into NFC Suspension This experiment can test the direct application of redispersion additives into NFC suspensions. In this experiment, a 2.1 wt % NFC slurry can be diluted to 0.1 wt % with tap water and stirred slowly for at least five hours to fully disperse the NFC fibers. 50 mL aliquots of the dilute NFC suspension can be measured and treated individually by direct addition of the exemplary redispersion additives. Each additive can be mixed directly into 50 mL of 0.1 wt % NFC suspension on a stir plate for five minutes. The resulting mixtures can be dried in a BINDER forced convection oven at 110° C. Following the drying, the resulting dry fiber mats can be submerged in 80 mL of tap water and resuspended on a stir plate for five minutes. The resuspended material can be evaluated qualitatively, using the following criteria to assess the degree of redispersion:
  a) High redispersion efficacy: Complete detachment of the fiber mat from the beaker well and total breakup of clusters/clumps into discrete fibers, resulting in an opaque/translucent suspension with no visible clots.
  b) Medium redispersion efficacy: Moderate to complete detachment of fiber mat from beaker well with small/medium NFC clots (1-5 mm diameter) suspended in aqueous media.
  c) Low redispersion efficacy: Little to no detachment of fiber mat from beaker well and presence of medium/large NFC clots (>5 mm diameter) suspended in aqueous media.

Expected results for redispersion efficacy for selected redispersion additives are listed as follows:

HPC, HPMC, glycerol are expected to produce high redispersion efficacy, added at amounts between 100% and 300% of the weight of the NFCs in suspension.

Caffeine, ethylene diamine, tetraethylene pentamine, Dytek EP, MC, Luvskol Plus, DPnP, and TPnB are expected to produce medium redispersion efficacy, added at amounts between two times and five times the weight of NFCs in suspension.

Other additives are expected either to yield low redispersion efficacy and/or to require larger relative volumes of the additive to produce a medium degree of redispersion.

Example 2: Binary/Tertiary Direct Additive Application into NFC Suspension

NFC suspensions, similar to those described in Example 1, can be diluted, stirred, and measured into 50 mL aliquots for treatment. Two or three additives (binary or tertiary systems) can be combined to treat each NFC sample, following the methods set forth in Example 1. All treated samples can be dried and tested for redispersion following the same protocols as Example 1. Redispersion efficacy for binary and tertiary systems can be predicted for various combinations of additives, using the redispersion efficacy criteria set forth in Example 1 to evaluate the effect of each combination of additives on redispersion.

The additive combinations can be introduced into the NFC samples in various ratios. Additive combinations of HPC and HPMC in a 1:1 ratio can be added in an amount three times greater than the amount of the NFCs in the mixture, with an expected high redispersion efficacy. Additive combinations of HPMC and MC in a 1:1 ratio can be added in an amount three times greater than the amount of the NFCs in the mixture, with an expected high redispersion efficacy. Other possible combinations are expected to yield medium or low redispersion efficacy, and/or to require fairly large amounts of additives in proportion to the amount of NFCs being treated. Potential combinations of additives are listed below in Table 1, with their predicted redispersion efficacy.

TABLE 1

| Additives | Ratio of Additives in Combination | Ratio of Additives to NFCs for testing | Predicted Redispersion Efficacy |
|---|---|---|---|
| MC:HPC:HPMC | 1:1:1 | 3:1 | Medium |
| HPC:CMC | 1:1 | 6:1 | Medium |
| HPC:CMC | 1:1 | 3:1 | Medium |
| HPMC:CMC | 1:1 | 3:1 | Medium |
| MC:CMC | 1:1 | 3:1 | Medium |
| HPC:MC | 1:1 | 3:1 | Medium |
| HPC:PnP | 1:5 | 12:1 | Medium |
| HPC:PnB | 1:5 | 12:1 | Low |
| HPC:DPnP | 1:5 | 0.60 | Medium |
| HPC:TPnB | 1:5 | 0.60 | Medium |
| HPC:caffeine | 1:2 | 0.15 | Medium |
| HPC:2-butoxyethanol | 1:2 | 0.15 | Medium |
| 2-butoxyethanol:PnB | 1:1 | 1.00 | Low |
| 2-butoxyethanol:TPnB | 1:1 | 1.00 | Medium |
| 2-butoxyethanol:DPnP | 1:1 | 1.00 | Medium |
| 2-butoxyethanol:PnP | 1:1 | 1.00 | Low |

Example 3: Unary Treatment of Post-Filtered NFC

In this Example, a 1 L suspension of diluted NPC (0.3-1.0 wt %) can be prepared in accordance with Example 1, and combined with a dilute pulp suspension (0.3-0.75 wt %). The combined stock suspension can be aggressively mixed on a stir plate for 15 min, and then it can be filtered through a 70-mesh screen in a Buchner funnel draining into a 250 mL graduated cylinder to remove excess water, thereby forming an NFC/pulp mat on the mesh screen. Vacuum can be used to increase the final solids content of the NFC/pulp mat (~10 wt %). The resulting mat of NFC/pulp fibers can be thoroughly mixed with redispersion additives for testing, by mixing each selected additive into the filtered solids with a spatula in a separate beaker.

Additives for testing redispersion capabilities can include LCST polymers and non-volatile additives. LCST polymers or non-volatile additive candidates can first be dissolved into a concentrated aqueous solution (ranging from 5 wt %-40 wt %) prior to adding them to the NFC/pulp solids. These solutions, each containing a single additive, can then be added to the NFC/pulp solids material to treat them, using methods similar to those described in Example 1. All resulting samples of treated NFC/pulp mixtures can then be deposited into silicone molds of spherical hemispheres (1.5 cm diameter) and dried at 110° C., yielding consistent sample shape, size, and density for comparison purposes.

Redispersion of the samples can be performed as described in the Examples above. The redispersion efficacy criteria set forth above can be used to assess qualitatively the results of the redispersion tests. HPMC used in an amount of 1.5-2 times the amount of NFCs is expected to produce low or medium redispersal efficacy, while glycerol in an amount of 3-4 times the amount of NFCs is expected to produce high redispersion efficacy.

Example 4: Binary Treatment of Post-Filtered NFC

In this experiment, NFC and pulp suspensions can be prepared and filtered in accordance with Example 3. A treatment solution used to dose filtered solid fibers can be prepared to include two active additives, such as HPMC and glycerol or HPMC and 2-butoxyethanol. Various ratios of additives and amounts of additives vs amount of NFCs can be tested. It is anticipated that ratios of HPMC to glycerol between about 0.4:1 and 2:1 would yield a medium or high redispersion efficacy, using the criteria for qualitative results provided above, and a ratio of 0.6:1 of HPMC to 2-butoxyethanol would yield a medium redispersion efficacy. For the HPMC: glycerol additive mixtures, a larger additive-to-NFC ratio, for example 3:1, 4:1 or higher, would be expected to yield greater redispersion efficacy than lower relative amounts of additives to NFCs.

Materials used in Examples 5-6 include:
Corning stir plate
BINDER forced convection oven
NFC (2.1 wt % in water): Auburn University
Sigma Aldrich Chemicals
  Tri(propylene glycol) butyl ether (TPnB)
  Di(propylene glycol) propyl ether (DPnP)
  Propylene glycol butyl ether (PnB)
  Propylene glycol propyl ether (PnP)
  Butylene glycol ethyl ether
  Ethylene glycol monobutyl ether (2-butoxyethanol)
  Propylene glycol monomethyl ether acetate
  Propylene glycol diacetate
  Ethylene glycol diacetate Benzyl alcohol
1-heptanol
1-hexanol
Caffeine
Glycerol
Piperazine
Pyridine
Methylcellulose (MC)
Hydroxyethyl cellulose (HEC)
Hydroxypropyl cellulose (HPC)
Hydroxypropylmethyl cellulose (HPMC)
Poly(methyl vinyl ether)
Melamine
Triethanolamine
Dytek EP (1,3 diaminopentane)
Ethylenediamine
Diethylenetriamine
Tetraethylenepentamine
1,2-Diaminocyclohexane
Polyethyleneimine (PEI)
Ethylenediaminetetraacetic Acid (EDTA)
Sodium dodecyl sulfate (SDS)
Other chemicals
Luviskol Plus (polyvinylcaprolactam): BASF
Capryl glucoside: Amazon
Decyl glucoside: Amazon
Coco glucoside: Amazon Example 5: Treatment of Charged NCE Fibers This experiment tested the direct application of redispersion additives into NFC suspensions. Soy hull was the bio source for the NCE fibers (NFCs), and it was mechanically and chemically treated by Auburn University to create NFC suspensions at 2.1 wt % solids. Varying ratios, as set forth in Table 2 below of HPMC and glycerol were combined to form solutions for treating the 2.1 wt % NFC suspension directly. The highly viscous treated suspensions were subsequently spread over a silicone sheet at a thickness between 1 mm-3 mm and dried in the BINDER forced convection oven at 75° C., to yield NFC sheets.

The resulting treated and control NFC sheets were resuspended in glass vials with DI water at 5 wt % solids by shaking vigorously by hand for three minutes. The vials were then observed qualitatively for redispersion efficacy, with the results set forth in Table 2 below. The following descriptions of redispersion efficacy were used to designate the qualitative results observed from these redispersion tests.

Redispersion Efficacy:
a) High redispersion efficacy: Complete breakup of fiber sheet into discrete fibers, resulting in an opaque/translucent suspension with no visible clots.
b) Medium redispersion efficacy: Moderate breakup of fiber sheet with small/medium NFC clots (1-5 mm diameter) suspended in aqueous media.
c) Low redispersion efficacy: Little to no breakup of fiber sheet and presence of medium/large NFC clots (>5 mm diameter) suspended in aqueous media.

TABLE 2

| NFC (g) | Additives | Ratio of Additives | Total Additive Amount (g) | Redispersion Efficacy |
|---|---|---|---|---|
| 0.3 | None | N/A | N/A | Low |
| 0.3 | HPMC:Glycerol | 1:19 | 0.9 | Low |
| 0.3 | HPMC:Glycerol | 1:19 | 1.8 | Medium |
| 0.3 | HPMC:Glycerol | 19:1 | 0.9 | Medium |
| 0.3 | HPMC:Glycerol | 19:1 | 1.2 | Medium |
| 0.3 | HPMC:Glycerol | 19:1 | 1.5 | High |
| 0.3 | HPMC:Glycerol | 19:1 | 1.8 | High |

Example 6: Redispersion of Surfactant-Loaded Nanocellular Elements

This experiment utilized 2.1 wt % soy-hull-derived nanocellular element (NFC) suspension from Auburn University to serve as a carrier for a chemical of interest (in this case, surfactants) when redispersed in water. For this experiment, all NFC samples were dosed with redispersion additives at a ratio of 6:1 with NFC fibers. The redispersion additives consisted of HPMC and glycerol at a ratio of 19:1, respectively. Following the direct application of the binary redispersion additive solution to the 2.1 wt % NFC suspension to form a treated suspension, various surfactants were mixed, individually, into the treated suspension, with the resulting mixtures being dried, and tested for redispersibility according to the procedures outlined in Example 5. The redispersibility was observed qualitatively according to the redispersion efficacy criteria set forth in Example 5. Table 3 below lists the surfactants tested and their effects on NFC redispersion.

TABLE 3

| NFC (g) | Surfactant(s) | Ratio of Surfactants | Total Surfactant Amount (g) | Redispersion Efficacy |
|---|---|---|---|---|
| 0.3 | SDS | (only one surfactant used) | 0.09 | Low |
| 0.3 | SDS | (only one surfactant used) | 0.20 | Low |
| 0.3 | SDS | (only one surfactant used) | 0.32 | Medium |
| 0.3 | SDS | (only one surfactant used) | 0.45 | Medium |
| 0.3 | SDS | (only one surfactant used) | 0.60 | High |
| 0.3 | Capryl Glucoside | (only one surfactant used) | 0.11 | High |
| 0.3 | Capryl Glucoside | (only one surfactant used) | 0.23 | High |
| 0.3 | Capryl Glucoside | (only one surfactant used) | 0.37 | High |
| 0.3 | Capryl Glucoside | (only one surfactant used) | 0.70 | High |
| 0.3 | Coco Glucoside | (only one surfactant used) | 0.70 | Medium |
| 0.3 | Decyl Glucoside | (only one surfactant used) | 0.70 | Medium |
| 0.3 | SDS:Capryl Glucoside | 1:1 | 0.70 | High |
| 0.3 | SDS:Coco Glucoside | 1:1 | 0.70 | High |
| 0.3 | SDS:Decyl Glucoside | 1:1 | 0.70 | High |

Those samples that could be dried and redispersed with high redispersion efficacy yielded a thick surfactant-containing liquid that could be useful as a soap. The results suggest that certain surfactants can be incorporated into redispersible NFC sheets to permit reconstitution as liquid surfactant-containing materials for uses such as soaps, shampoos, and the like. It is hypothesized that other active agents (inter alia, bleaches, cationic surfactants for fabric softening, fragrances, emollients, etc.) can be analogously incorporated into redispersible NFC sheets as well, alone or in combination with other ingredients.

Materials used in Example 7 include:
Corning stir plate
Soy hull NFC (2.1 wt % in water) (Auburn University)
Butcher paper—uncoated (Amazon)
DI water
Carrington Farms organic coconut cooking oil
Oven
Baking Pan
Sigma Aldrich Chemicals
   Glycerol
   Methyl cellulose (MC)

Example 7: Oil and Grease Resistance

This experiment tested the ability of treated NFC to impart oil and grease resistance onto food contact paper. A soy hull NFC suspension (2.1% concentration) was used in this experiment. A 4.5% stock solution of MC and glycerol in DI water was made on the stir plate, with 95% of the actives being HPMC and 5% being glycerol. 5-gram samples of the 2.1% soy hull NFC suspension were added to three small beakers, and corresponding amount of MC/glycerol solution was added in with the NFC suspension, leading to a 3:1, 6:1, and 9:1 treatment of active dispersant to dry NFC. The 3:1 sample included 7 grams of the 4.5% MC/glycerol solution, the 6:1 sample included 14 grams of the MC/glycerol solution, and the 9:1 sample included 21 grams of the MC/glycerol solution. There was also a sample with 5 grams of 2.1% NFC suspension without any HPMC/glycerol treatment, but 7 grams of additional DI water was added to ensure a less viscous coating and to better match the viscosity of the other samples. This was treated as a control sample. The suspensions were mixed by hand and set aside.

Separately, uncoated brown butcher paper was cut up into small, 1.5" by 1.5" squares. The four suspensions made in the previous step were each poured into its own weigh boat, and three different butcher paper squares were submerged (one at a time) in each suspension. Once each square was fully submerged and fully coated, it was removed with tweezers and held above the weight boat for one minute to allow excess suspension to run off the paper. Each piece of butcher paper was then put in the oven to dry at 75° C. for 30-60 minutes. After the squares were fully dry, three drops each of DI water and liquid coconut oil were dropped onto each square. The squares were observed at two intervals: immediately after the droplets of the water and oil were applied (Time 1), and 15 minutes after the droplets were applied (Time 2). When observed at Time 1 (immediately after the drops were applied), all four samples appeared to repel water. The water droplets held their shape, and the contact angle (observed qualitatively) was relatively high and had non-wetting characteristics. No color change occurred on the brown butcher paper below the water droplet, indicating that the water droplet did not penetrate the pores of the butcher paper. When observed at Time 1, the oil droplets on the control sample had a contact angle (qualitatively observed) close to zero, as no droplet stayed present above the paper. The droplet spread out to a large area (roughly 3× the size of the droplet), and the paper became wet and darker brown in color, indicating that the oil penetrated the pores of the paper. The 3:1 treated sample had a slightly higher contact angle than the control sample, as the droplet remained visible, and the darker brown spot below the droplet was smaller than the control, roughly double the size of the original droplet. The contact angle of the oil droplet on the 6:1 sample was slightly higher than the one on the 3:1 sample, but otherwise looked about the same. The oil droplet on the 9:1 sample had the highest contact angle of all samples, and no dark brown spot appeared below the droplet, indicating that the oil did not penetrate the pores of the butcher paper. When observed at Time 2 (15 minutes after the droplets were applied), the water droplets remained the same as described previously for all samples. When observed at Time 2, the appearance of the oil droplets had changed. The brown spot from the oil droplets from the control sample and the 3:1 sample had grown to cover about one third the area of the square, indicating increased wetting over time. The contact angle of the oil droplets on the 6:1 sample had decreased over time, and the brown spot from the droplets had grown to cover about one fifth of the area of the square. However, for the 9:1 sample, the oil droplet size and contact angle and lack of dark brown spot remained unchanged at Time 2, indicating sustained non-wetting over time.

Materials used in Example 8 include:
Corning stir plate
NFC suspension (2.1 wt % in water) (Auburn University)
DI water
Revlon blow dryer
Hair ties
Tape
Stirring bar receiver
Full Shine Remy human hair: Amazon
Sigma Aldrich Chemicals
   Glycerol
   Low molecular weight chitosan
   Hydroxypropylmethyl cellulose (HPMC)
   Acetic Acid
Other chemicals
   Xiameter OFX-0193 PEG-12 dimethicone: Dow Chemical Example 8: NFC Hair Hold This experiment tested the ability of treated NFC to aid in hair hold and replace the use of hairspray and harsh chemicals. An NFC suspension (2.1% concentration) was used in this experiment. A 9.43% solution of HPMC and glycerol was made, containing 90.57% DI water; a 100 gm stock solution was made, containing 9.43 grams of HPMC/glycerol (8.96 grams of HPMC and 0.47 grams of glycerol), and 90.57 g of DI water; this solution, in which 95% of the actives were HPMC and 5% were glycerol, was the HPMC/glycerol solution used as follows: 5.95 grams of the 2.1% NFC suspension was added to a small beaker, and 3.98 grams of the HPMC/glycerol solution was added in with the NFC suspension, leading to a 3:1 ratio of active dispersant to dry NFC. The suspension was mixed by hand and set aside.

Separately, a 1% low molecular weight chitosan solution was made, comprising NFC in 1% acetic acid. To do this, 40.06 grams of DI water was added to the beaker with the NFC suspension (previously treated with the HPMC/glycerol solution previously prepared) for further dilution. Then, 0.5 grams of acetic acid was added dropwise into the beaker and stirred on a stir plate. 0.5 grams of chitosan powder was slowly added to the beaker while the suspension stirred vigorously. The suspension was left to stir for about an hour until the suspension looked homogeneous. Once the chitosan appeared to be fully dissolved, 2.5 grams of Xiameter OFX-0193 PEG-12 dimethicone from Dow Chemical was added to the beaker and stirred for a few seconds. This formulation was set aside for testing as a hair treatment.

The formulation was then tested against a control sample to validate efficacy as a hair treatment. Two samples of 0.5 grams of hair were cut from the Full Shine Remy human hair wig. Each sample was cut to be 12 inches in length. Each sample was tied at one end with a small hair tie and secured to a table with tape. Each sample of hair was thoroughly wet with DI water until no dry hair remained. The control hair sample was left wet with water only, and the experimental hair sample was then wet with 0.2 grams of the previously described hair treatment. The hair treatment was applied with a syringe, and then thoroughly rubbed through the length of the hair sample. Both samples were then curled up tightly around a stirring bar receiver and blow dried for 3 minutes. After the three minutes, the stirring receiver was removed from the hair, and the curls were observed. The curls were also observed after pinching the curls along the length of hair to stretch them out 3 to 4 times.

Results immediately after blow drying the control and experimental samples showed similar curls. Curls were very tight, with ringlets precisely the size of the diameter of the stirring bar receiver. The control sample showed strands of hair that were slightly less tight than those of the experimental sample, with slightly more space in between each strand of hair. After pinching the hair and stretching it out, the control sample ringlets became farther apart, and did not provide any "bounce back." The diameter of the ringlets grew to nearly double the size of the diameter of the stirring bar receiver, and the hair became frizzy, with each strand now farther apart from each other. The experimental sample bounced back to its original shape, with no change in ringlet diameter, space between the ringlets, or space between hair strands. All curls from both the control and experimental samples were soft to the touch with no "crispiness."

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method of producing an article of manufacture comprising a redispersible, dried nanocellulose (NC)-containing matrix with nanocellulose elements (NCEs) embedded therein and an active agent, wherein the active agent is a household product or a laundry product, the method comprising:
    drying a liquid formulation to form the redispersible, dried NC-containing matrix, wherein the liquid formulation comprises a suspension of the nanocellulose elements (NCEs) in a liquid medium and a drying/dispersal additive, wherein the drying/dispersal additive is a volatile small molecule additive or a blocking agent and wherein the drying/dispersal additive disrupts hydrogen bonding between the nanocellulose elements during the drying;
    wherein the redispersibility of the dried NC-containing matrix is greater than that of a dried control matrix prepared by drying a control suspension of the nanocellulose elements in the liquid medium, wherein the control suspension lacks the drying/dispersal additive, and
    wherein the redispersible, dried NC-containing matrix comprises interstices and wherein the active agent is disposed within the interstices of the matrix, wherein the active agent is dispersed on the surface of the matrix, or
    wherein the active agent is enclosed by the matrix;
    wherein the volatile small molecule additive is selected from the group consisting of tri(propylene glycol) butyl ether, di(propylene glycol) propyl ether, propylene glycol butyl ether, propylene glycol propyl ether, ethylene glycol monobutyl ether, propylene glycol monomethyl ether acetate, propylene glycol diacetate, ethylene glycol diacetate, benzyl alcohol, 1-heptanol, 1-hexanol, ethylene diamine, diethylene triamine, tetraethylene pentaamine, 1,3-pentane diamine, piperazine, 1,2-cyclohexane diamine, aniline, pyridine, and piperazine; and
    the blocking agent is selected from the group consisting of a purine, a pyrimidine, a humectant, and a fatty acid.

2. The method of claim 1, wherein the active agent is the laundry product, and the laundry product is selected from the group consisting of bleaches, laundry detergents, enzymes, fabric softeners, static reducers, and fragrances.

3. The method of claim 2, wherein the active agent is selected from the group consisting of laundry detergents, enzymes, and bleaches.

4. The method of claim 2, wherein the active agent is selected from the group consisting of fabric softeners, static reducers, and fragrances, and wherein the active agent is applied as a waxy layer to the matrix, wherein the waxy layer is capable of melting in a hot dryer to release the active agent from the waxy layer.

5. The method of claim 1, wherein the nanocellulose elements are cellulose nanofibers or cellulose microfibers.

6. The method of claim 1, wherein the drying/dispersal agent is the volatile small molecule additive.

7. The method of claim 1, wherein the drying/dispersal additive is the blocking agent.

8. The method of claim 7, wherein the blocking agent comprises nanoscale particulate material.

9. The method of claim 7, wherein the blocking agent is a purine or a pyrimidine.

10. The method of claim 9, wherein the blocking agent is a purine, and wherein the purine is a xanthine or a xanthine derivative.

11. The method of claim 7, wherein the blocking agent is a humectant.

12. The method of claim 11, wherein the humectant is selected from the group consisting of glycerin, caprylyl glycol, ethylhexylglycerin, tribehenin, hydrolyzed soy protein, propylene glycol, methyl gluceth-20, phenyl trimethicone, hyaluronic acid, sorbitol and gelatin.

13. The method of claim 7, wherein the blocking agent is a fatty acid.

14. The method of claim 13, wherein the fatty acid is selected from the group consisting of stearic acid, palmitic acid, myristic acid, lauric acid, capric acid, caprylic acid, and caproic acid.

15. The method of claim 1, wherein the active agent is disposed within the interstices of the redispersible, dried NC-containing matrix.

16. The method of claim 1, wherein the active agent is dispersed on the surface of the redispersible, dried NC-containing matrix.

17. The method of claim 1, wherein the redispersible, dried NC-containing matrix is shaped as at least one dried sheet.

18. The method of claim 17, wherein the at least one dried sheet is a plurality of dried sheets in a layered arrangement.

19. The method of claim 18, wherein the active agent is dispersed on the surface of one or more of the dried sheets in the layered arrangement.

20. The method of claim 1, wherein the redispersible, dried NC-containing matrix encloses the active agent.

21. The method of claim 20, wherein the laundry product is a laundry detergent or wherein the household product is a cleaning product, and wherein the redispersible, dried NC-containing matrix encloses a paste or a gel comprising the laundry detergent or the cleaning product, and wherein the paste or gel further comprises a second active agent selected from the group consisting of bleaches, enzymes for stain removal, and fabric softeners.

22. The method of claim 20, wherein the laundry product is a laundry detergent or wherein the household product is a cleaning product, and wherein the redispersible, dried NC-containing matrix encloses a paste or a gel comprising the laundry detergent or the cleaning product, and wherein the paste or gel is formed by suspending the laundry detergent or cleaning product in a vehicle formed from a water-soluble, non-aqueous viscous liquid polymer.

23. The method of claim 22, wherein the viscous liquid polymer is selected from the group consisting of polypropylene glycol, polyethylene glycol, polyethylene oxide, and polyoxyethylene.

24. The method of claim 22, wherein the paste or gel further comprises a thickening agent that is soluble in the water-soluble non-aqueous viscous liquid polymer.

25. The method of claim 24, wherein the paste or gel further comprises a plasticizer.

26. The method of claim 25, wherein the plasticizer is a hygroscopic plasticizer.

27. The method of claim 26, wherein the hygroscopic plasticizer is glycerol.

* * * * *